US006587728B2

(12) United States Patent
Fang et al.

(10) Patent No.: US 6,587,728 B2
(45) Date of Patent: Jul. 1, 2003

(54) SYSTEMS AND METHODS FOR PERFORMING PROSTHETIC OR THERAPEUTIC NEUROMUSCULAR STIMULATION USING AN EXTERNAL, BATTERY POWERED CONTROLLER WITH POWER CONSERVATION FEATURES

(75) Inventors: Zi-Ping Fang, Mayfield Village, OH (US); Geoffrey B Thrope, Shaker Heights, OH (US); Anthony Ignagni, Oberlin, OH (US); Soheyl Pourmehdi, Beachwood, OH (US); Dustin Tyler, Richmond Heights, OH (US); Robert B Strother, Jr., Willoughby Hills, OH (US); Maria E Walker, Shaker Heights, OH (US); Trisha L Winter, Cleveland Heights, OH (US); Jeffrey A Demchak, Parma, OH (US); Joe Mrva, Willoughby, OH (US); Anthony Szpak, Rocky River, OH (US)

(73) Assignee: NeuroControl Corporation, Valley View, OH (US)

( * ) Notice: Subject to any disclaimer, the term of this patent is extended or adjusted under 35 U.S.C. 154(b) by 0 days.

(21) Appl. No.: 09/822,779

(22) Filed: Mar. 30, 2001

(65) Prior Publication Data

US 2002/0183803 A1 Dec. 5, 2002

(51) Int. Cl.[7] ................................................ A61N 1/372
(52) U.S. Cl. ............................. 607/48; 607/40; 607/41
(58) Field of Search ............................. 607/16, 29, 39, 607/40, 41, 42, 49

(56) References Cited

U.S. PATENT DOCUMENTS

| | | | |
|---|---|---|---|
| 4,413,314 A | 11/1983 | Slater et al. | |
| 4,942,514 A | 7/1990 | Miyagaki et al. | |
| 4,990,258 A | 2/1991 | Bjare et al. | |
| 5,167,229 A | 12/1992 | Peckham et al. | |
| 5,247,434 A | 9/1993 | Peterson et al. | |
| 5,285,781 A | 2/1994 | Brodard | |
| 5,300,096 A | 4/1994 | Hall et al. | |
| 5,581,687 A | 12/1996 | Lyle et al. | |
| 5,609,770 A | 3/1997 | Zimmerman et al. | |
| 5,653,887 A | 8/1997 | Wahl et al. | |
| 5,861,017 A | 1/1999 | Smith et al. | |
| 5,983,140 A | 11/1999 | Smith et al. | |
| RE36,690 E | * 5/2000 | McGraw et al. | |
| 6,163,725 A | * 12/2000 | Peckham et al. | |
| 6,315,721 B2 | 11/2001 | Schulman et al. | |

OTHER PUBLICATIONS

NeuroControl Press Release; Jan. 2000; StIM™ System Receiver CE mark approval.
NeuroControl StIM™ System Brochure; circa Jan. 2000.
The NeuroControl StIM™ System Brochure; circa Jan. 2000.

* cited by examiner

*Primary Examiner*—Scott Getzow
(74) *Attorney, Agent, or Firm*—Ryan Kromholz & Manion, S.C.

(57) ABSTRACT

The systems and methods provide effective neuromuscular stimulation to meet a host of different prosthetic or therapeutic objections. The systems and methods also provide convenience of operation, flexibility to meet different user-selected requirements, and transportability and ease of manipulation, that enhance the quality of life of the individual that requires chronic neuromuscular stimulation.

21 Claims, 35 Drawing Sheets

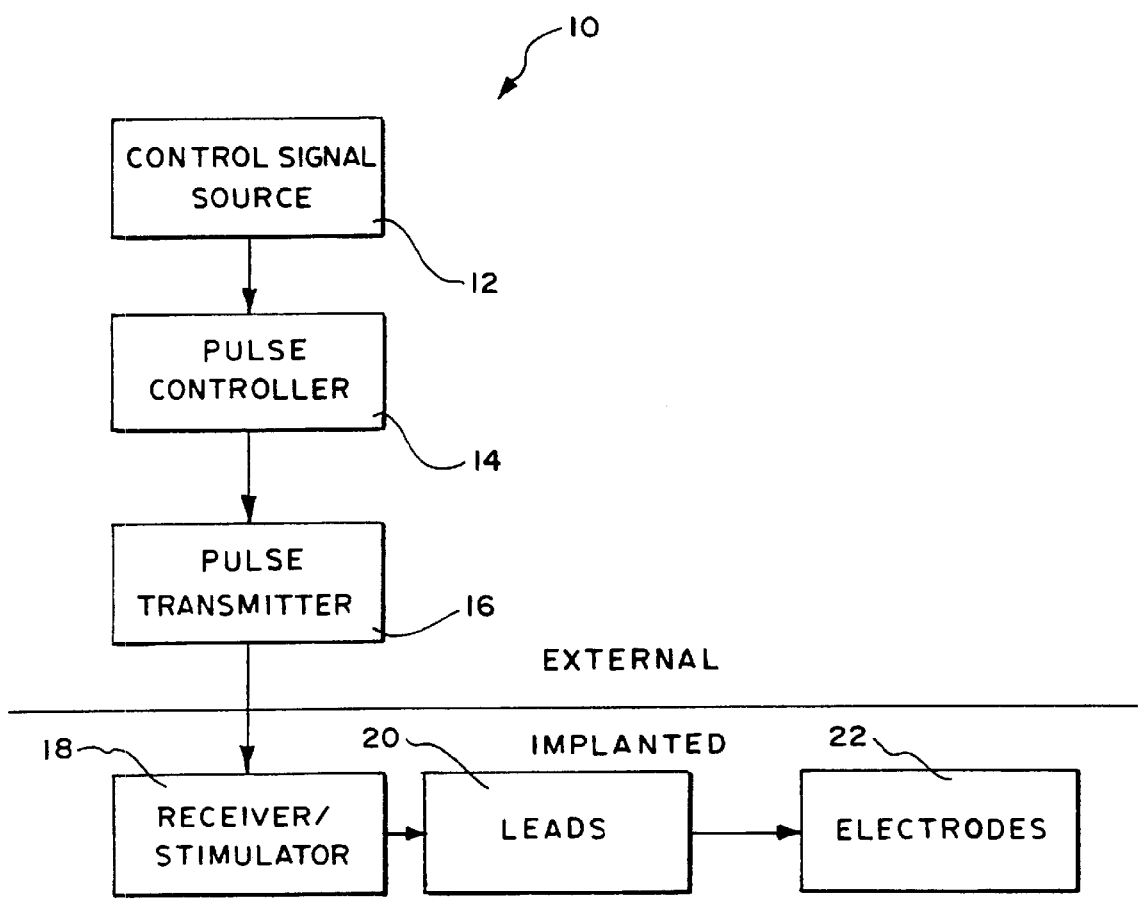

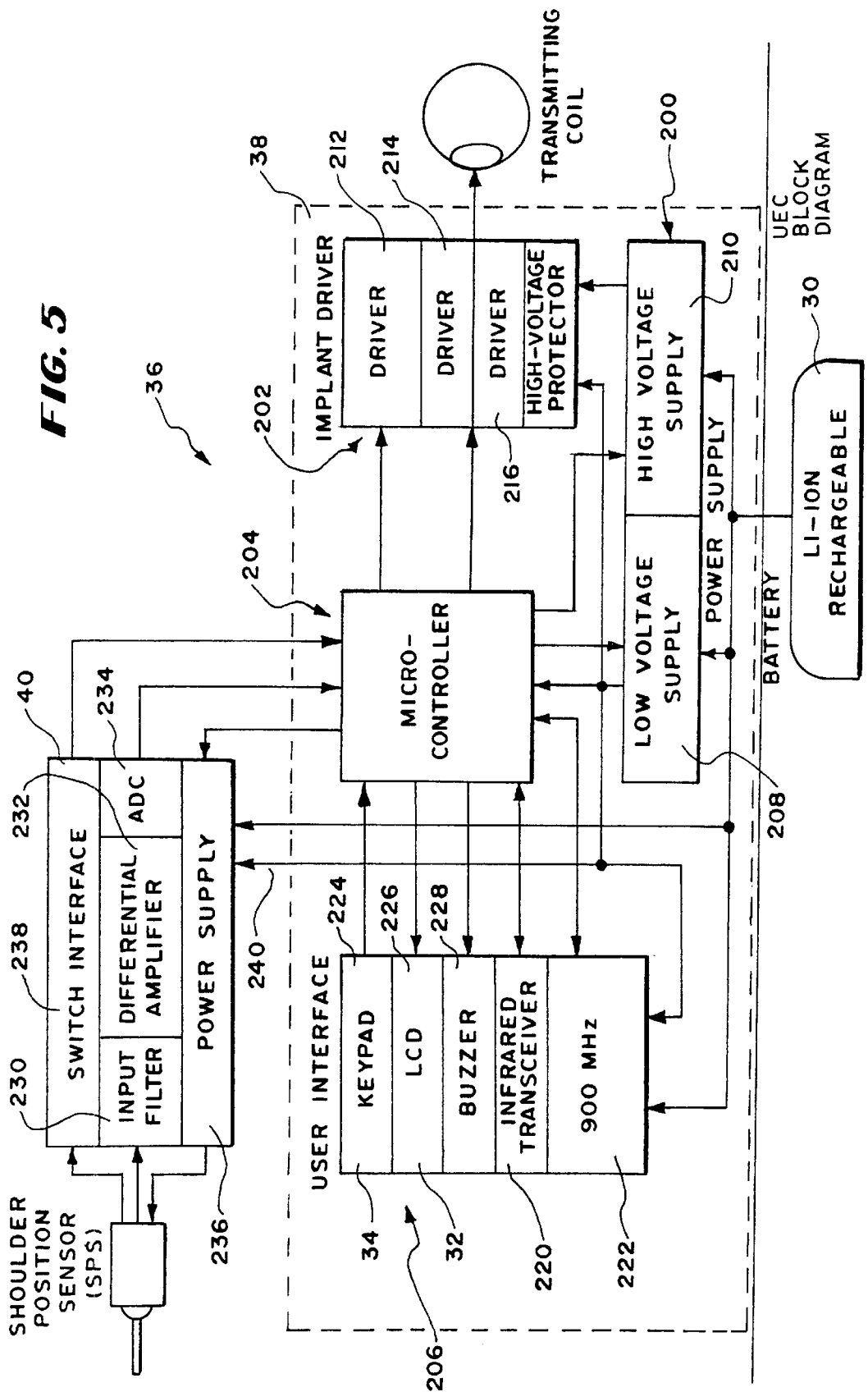

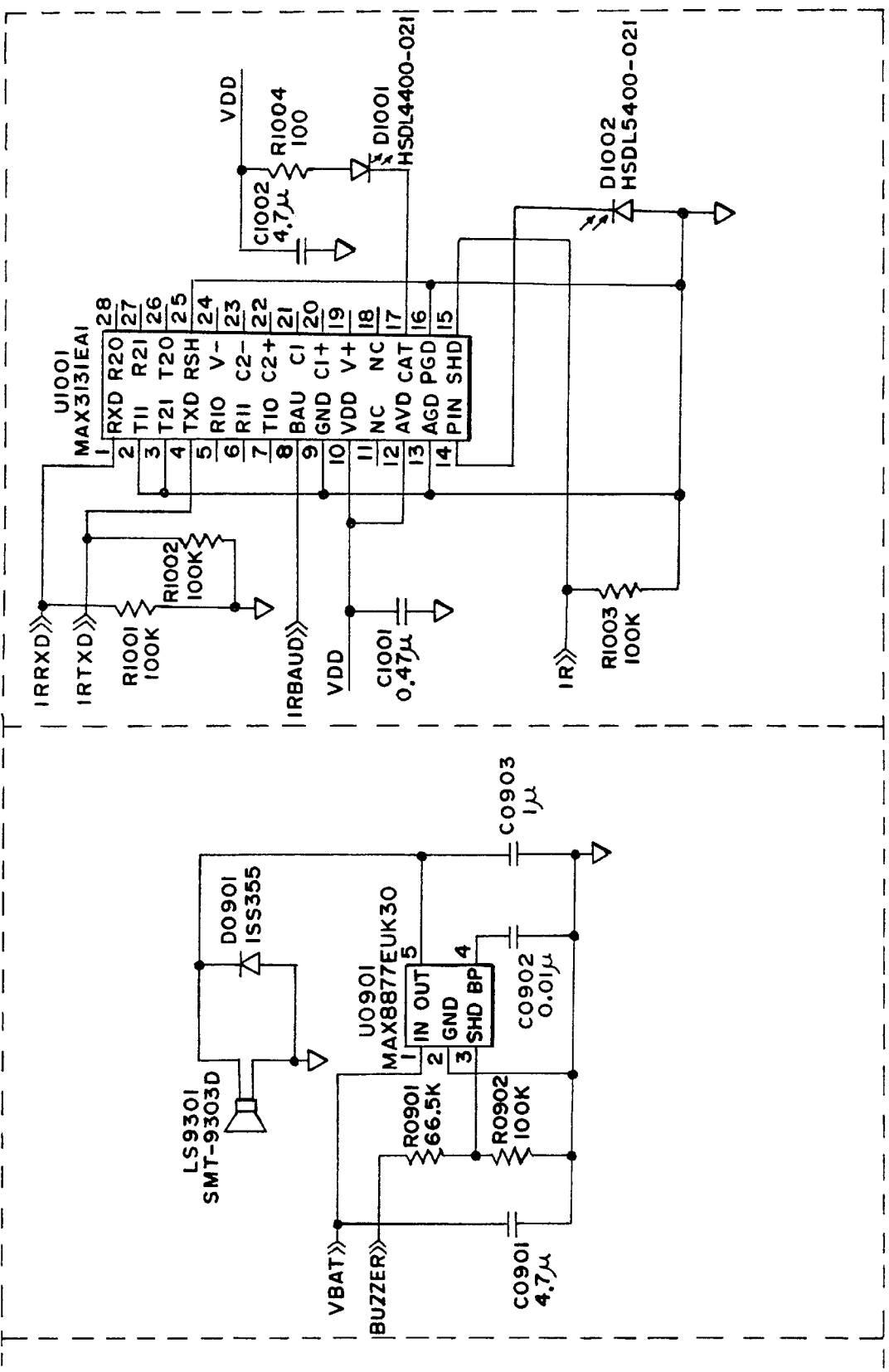

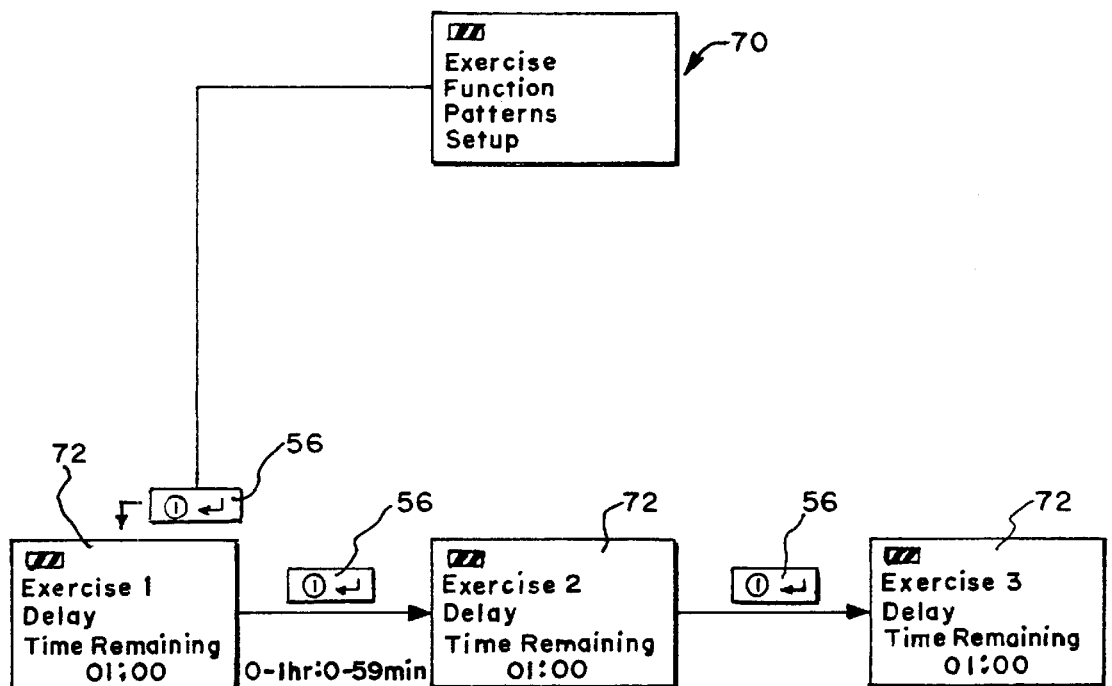
FIG. 6
FIG. 7
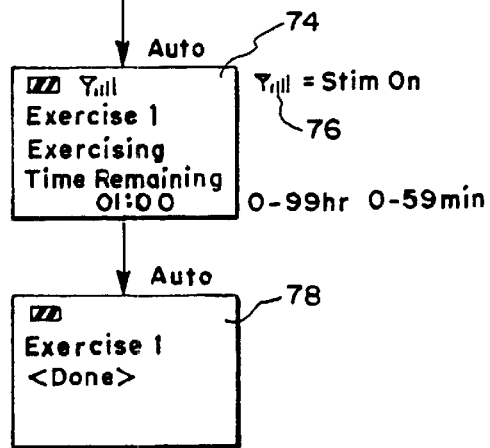

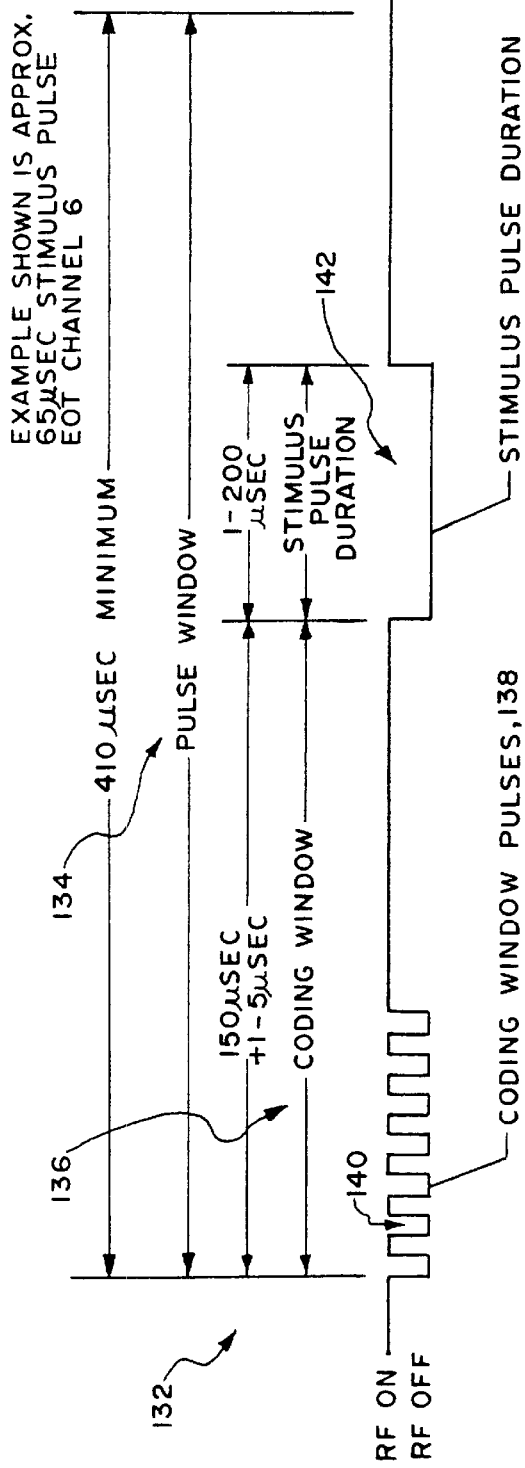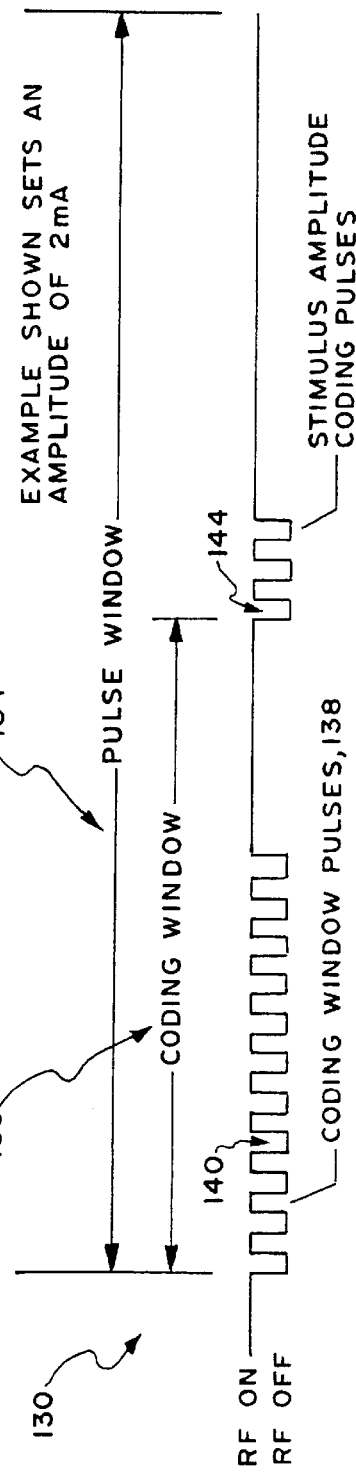

SYSTEMS AND METHODS FOR PERFORMING PROSTHETIC OR THERAPEUTIC NEUROMUSCULAR STIMULATION USING AN EXTERNAL, BATTERY POWERED CONTROLLER WITH POWER CONSERVATION FEATURES

FIELD OF THE INVENTION

This invention relates to systems and methods for providing function to otherwise paralyzed muscles.

BACKGROUND OF THE INVENTION

Functional Electrical Stimulation or Function Neuromuscular Stimulation, in short hand, typically refer to prosthetic systems and methods that restore function to muscles in the body that are otherwise paralyzed due to lack of neuromuscular stimulation, e.g., due to spinal cord injury, stroke, or disease. These conditions can break or otherwise disrupt the path or paths by which electrical signals generated by the brain normally travel to neuromuscular groups, to stimulate coordinated muscle contraction patterns. As a result, even though the nerves and muscles are intact, no electrical stimulation is received from the spinal cord, and the associated muscles do not function. Such systems and methods replace the disrupted, physiologic electrical paths, and restore function to the still intact muscles and nerves. Such systems and methods are known, e.g., to restore finger-grasp functions to muscles in the arm and hand, or to restore bladder and bowel control to muscles in the bladder, urethral sphincter, and bowel or to restore a standing function to muscles in the hip and thigh.

Neuromuscular stimulation can perform therapeutic functions, as well. These therapeutic functions provide, e.g., exercise to muscle, or pain relief for stroke rehabilitation, or other surgical speciality applications, including shoulder subluxation, gait training, etc.

While existing systems and methods provide remarkable benefits to individuals requiring neuromuscular stimulation, many quality of life issues still remain. For example, existing systems are function specific, meaning that a given device performs a single, dedicated stimulation function. An individual requiring or desiring different stimulation functions is required to manipulate different function specific stimulation systems. Such systems are not capable of receiving control inputs from different sources, or of transmitting stimulation outputs to different stimulation assemblies. Concurrent performance of different stimulation functions is thereby made virtually impossible.

Furthermore, the controllers for such function specific systems are, by today's standards, relatively large and awkward to manipulate and transport. They are also reliant upon external battery packs that are themselves relatively large and awkward to transport and recharge.

While the controller can be programmed to meet the individual's specific stimulation needs, the programming requires a trained technical support person with a host computer that is physically linked by cable to the controller. The individual requiring neuromuscular stimulation actually has little day to day control over the operation of the controller, other than to turn it on or turn it off. The individual is not able to modify operating parameters affecting his/her day-to-day life.

It is time that systems and methods for providing neuromuscular stimulation address not only specific prosthetic or therapeutic objections, but also address the quality of life of the individual require neuromuscular stimulation.

SUMMARY OF THE INVENTION

The invention provides improved systems and methods for providing prosthetic or therapeutic neuromuscular stimulation.

One aspect of the invention provides neuromuscular stimulation systems and methods that are readily transported by the user. In one embodiment, the systems and methods employ a controller that incorporates within a housing an output device that can be coupled to an electrode and a microprocessor that is coupled to the output device. The microprocessor includes a processing element operative to generate a signal pattern to an electrode to control at least one neuromuscular stimulation function. According to this aspect of the invention, a battery is also carried by the housing and coupled to the microprocessor to power the processing element. In one embodiment, the housing and battery are sized and configured, when coupled to the microprocessor, to fit within a hand of an individual or to otherwise be carried by an individual.

The battery is desirably rechargeable. Desirably, the battery is removable from the housing for recharging and can be recharged only when removed from the housing.

Another aspect of the invention provides a controller to provide functional neuromuscular stimulation. The controller comprises a housing and an output device carried by the housing that can be coupled to an electrode. The controller also includes a signal source to generate a control signal and an input device carried by the housing to receive the control signal generated by the signal source. A microprocessor is carried by the housing and is coupled to the output device and the input device. The microprocessor includes a processing element operative to generate a signal pattern to an electrode to control at least one neuromuscular stimulation function in response to a control signal received from the input device. The controller further includes a battery carried by the housing and coupled to the microprocessor to power the processing element. According to this aspect of the invention, the control signal generated by the signal source comprises a periodic succession of pulses to conserve battery life.

Another aspect of the invention provides a controller to provide functional neuromuscular stimulation. The controller comprises a housing and an output device carried by the housing that can be coupled to an electrode. A microprocessor is carried by the housing and is coupled to the output device. The microprocessor includes a processing element operative to generate a signal pattern to an electrode to control at least one neuromuscular stimulation function. The controller also includes a battery carried by the housing and coupled to the microprocessor to power the processing element. According to this aspect of the invention, the signal pattern generated by the processing element comprises command signals transmitted in a periodic succession of energy pulses to conserve battery life.

In one embodiment, each command signal includes a sequence of periodic pulses to identify an electrode channel, or a set stimulation amplitude command for the identified electrode channel, or a set stimulation duration command for the identified electrode channel, or combinations thereof.

In one arrangement, the sequence of periodic pulses comprises an energy on period, an energy off period, and gaps between successive energy on and energy off periods. In this arrangement, by number and sequence of gaps, a code is expressed that identifies an electrode channel, or a set stimulation amplitude command for the identified electrode, or a set stimulation duration command for the identified electrode, or combinations thereof.

In one embodiment, the periodic succession of energy pulses comprises modulated radio frequency waves.

In use, the systems and methods can be used, e.g., to affect at least one motor function, or to affect a bladder or bowel control function, or to affect an erection control function, or to affect combinations thereof. The systems and methods can be used to affect at least two neuromuscular stimulation functions, either concurrently or independently.

The systems and methods that embody the features of the various aspects of the invention provide effective neuromuscular stimulation to meet a host of prosthetic or therapeutic objections. The systems and methods also provide convenience of operation, flexibility to meet different user-selected requirements, and transportability and ease of manipulation, that enhance the quality of life of the individual that requires chronic neuromuscular stimulation.

Other features and advantages of the inventions are set forth in the following specification and attached drawings.

BRIEF DESCRIPTION OF THE DRAWINGS

FIG. 1 is a diagrammatic view of a system that makes possible the restoration of function to muscles in the body that are otherwise paralyzed due to lack of neuromuscular stimulation;

FIG. 5 is a representative circuit block diagram for the microprocessor housed within the universal external controller shown in FIGS. 3A to 3C;

FIGS. 5A to 5M are schematic circuit diagrams of the principal circuit components of the microprocessor housed within the universal external controller shown in FIGS. 3A to 3C;

FIG. 6 is a view of an opening screen of the user interface that the microprocessor shown in FIG. 5 generates, prompting the user to select from a list of different stimulation functions that the universal external controller enables;

FIG. 7 is a view of the hierarchy of the Exercise Regime screens of the user interface that the microprocessor shown in FIG. 5 generates, prompting the user to select from a list of different exercise stimulation functions that the universal external controller enables;

FIGS. 14A to 14D are diagrammatic views of the pulsed output command signals that the universal controller generates to conserve power and, thus, conserve battery life.

Figure 2:
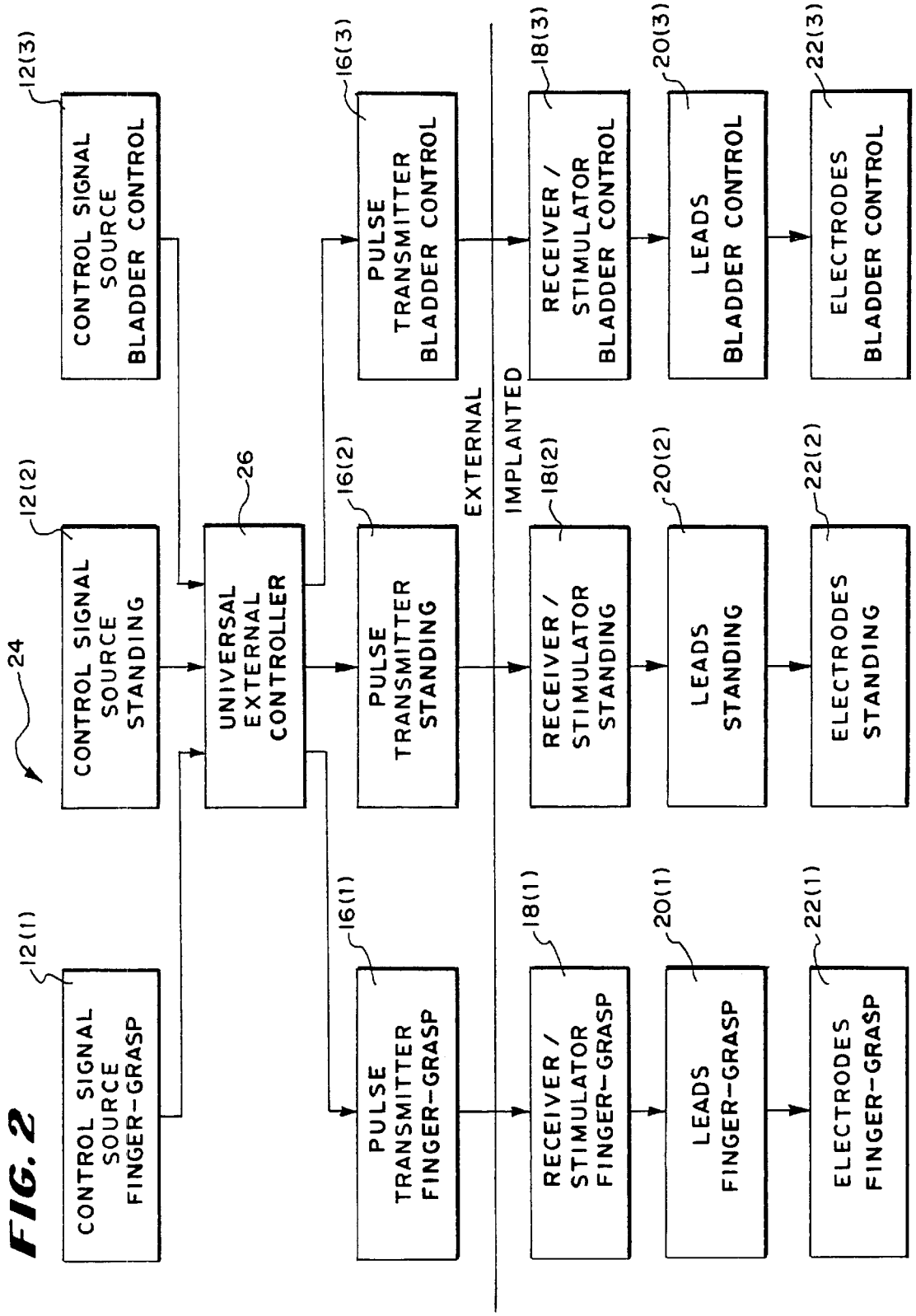
FIG. 2 is a diagrammatic view of a system that supports multiple prosthetic or therapeutic objectives, using a universal external controller, for achieving (i) a hand-grasp function in upper extremity arm muscles; (ii) a standing function in lower extremity leg muscles; and (iii) a bladder and bowel control function.
Figure 3A:
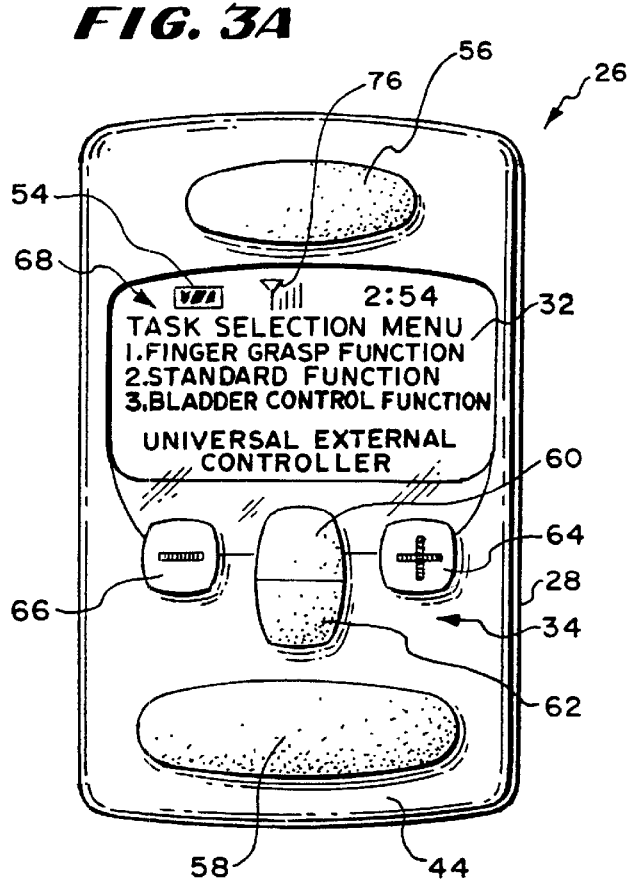
FIG. 3A is a front view of the universal external controller shown in FIG. 2, showing the interface screen by which the user can select one or more neuromuscular stimulation functions.
Figure 3B:
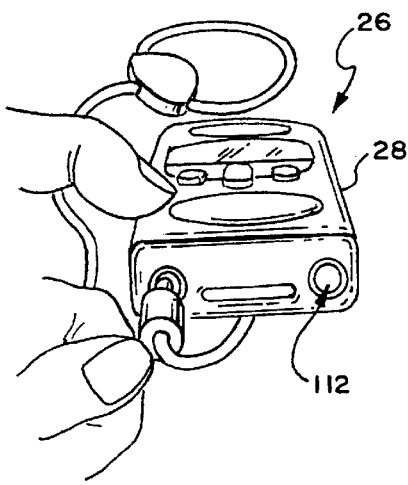
FIG. 3B is a bottom view of the universal external controller shown in FIG. 3A, showing the outputs for connecting different function-specific neuromuscular stimulation assemblies to the controller.
Figure 3C:
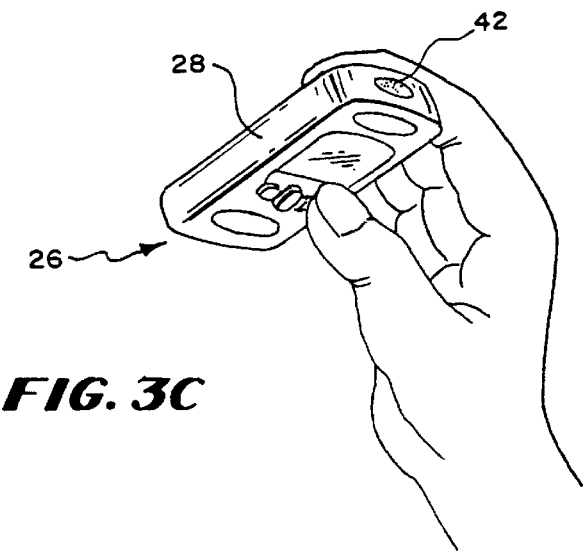
FIG. 3C is a perspective view of the universal external controller shown in FIG. 3A, demonstrating how the compact size and configuration of the controller makes it well suited for hand-held operation.
Figure 4:
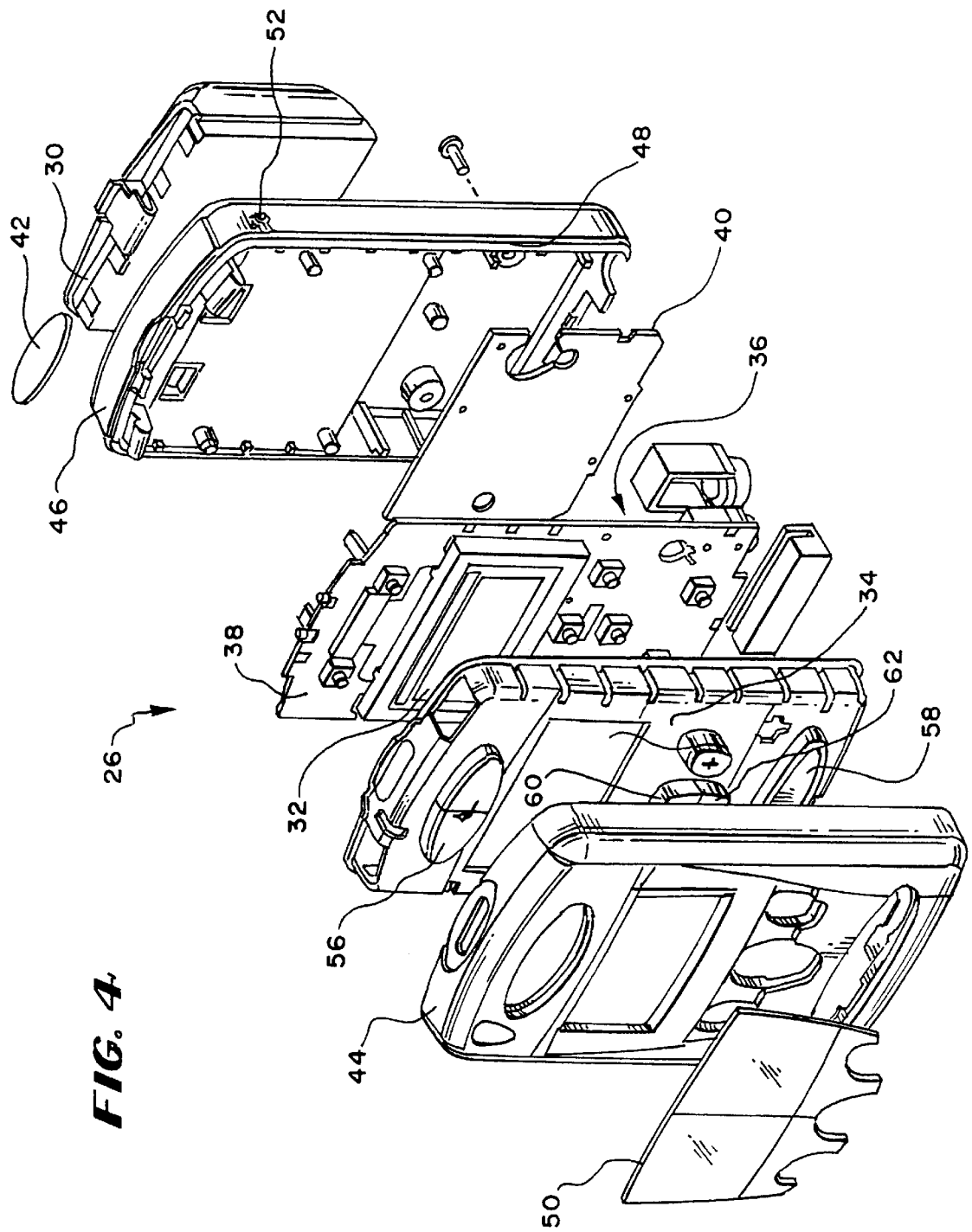
FIG. 4 is an exploded perspective view of the universal external controller shown in FIGS. 3A to 3C.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with providing functional neuromuscular stimulation for prosthetic or therapeutic purposes. That is because the features and advantages that arise due to the invention are well suited to this purpose. Still, it should be appreciated that the various aspects of the invention can be applied to achieve other objectives as well.

I. System for Providing Functional Neuromuscular Stimulation Using a Universal External Controller FIG. 1 shows a system 10 that makes possible the restoration of function to muscles in the body that are otherwise paralyzed due to lack of neuromuscular stimulation, e.g., due to spinal cord injury or stroke. Spinal cord injury or stroke can break or otherwise disrupt the path or paths by which electrical signals generated by the brain normally travel to neuromuscular groups, to stimulate coordinated muscle contraction patterns. As a result, even though the nerves and muscles are intact, no electrical stimulation is received from the spinal cord, and the associated muscles do not function.

In use, the system 10 generates and distributes electrical current patterns to one or more targeted neuromuscular regions. The resulting patterns of neuromuscular stimulation restore desired muscle function in the targeted region or regions. The stimulatation can be achieved by direct application of electrical current to a nerve (e.g., using a nerve cuff electrode), or by indirect distribution of electrical current to a nerve through adjacent muscle tissue (e.g., using epimysial or intramuscular electrodes).

As will be described in greater detail later, the system 10 can restore function to a single, targeted neuromuscular region, for example, to upper extremity muscles in the arm, e.g., to restore hand-grasp functions; or to lower extremity muscles in the leg, to restore standing or ambulatory functions; or to bladder and bowel muscles, to restore micturition; or to muscles controlling (in males) erection and ejaculation, or (in females) lubrication, to restore sexual or reproductive function. The system 10 can also be selectively operated to restore function to more than one targeted neuromuscular region, making it possible for an otherwise paralyzed individual to use the system 10 to selectively perform not only hand-grasp functions, but also to selectively perform standing/ambulatory and/or bladder and bowel control functions and/or other stimulation functions, as well.

The system 10 comprises basic functional components that can be assembled and arranged to achieve single or several neuromuscular stimulation functions. Generally speaking, as shown in FIG. 1, the basic functional components for a prosthetic neuromuscular stimulation function include (i) a control signal source 12; (ii) a pulse controller 14; (iii) a pulse transmitter 16; (iv) a receiver/stimulator 18; (v) one or more electrical leads 20; and (vi) one or more electrodes 22.

As assembled and arranged in FIG. 1, the control signal source 12 functions to generate an output, typically in response to some volitional action by a patient, or a trained partner, or another care giver. In response to the output, the pulse controller 14 functions according to preprogrammed rules or algorithms, to generate one or more prescribed stimulus timing and command signals.

The pulse transmitter 16 functions to transmit these prescribed stimulus timing and command signals, as well an electrical operating potential, to the receiver/stimulator 18. The receiver/stimulator 18 functions to distribute electrical current patterns according to the prescribed stimulus timing and command signals, through the leads 20 to the one or more electrodes 22. The one or more electrodes 22 store electrical energy from the electrical operating potential and function to apply electrical current patterns to the targeted neuromuscular region, causing the desired muscle function.

The basic functional components can be constructed and arranged in various ways. In a representative implementation, some of the components, e.g., the control signal source 12, the pulse controller 14, and the pulse transmitter 16 comprise external units manipulated outside the body. In this implementation, the other components, e.g., the receiver/stimulator 18, the leads 20, and the electrodes 22 comprise implanted units placed under the skin within the body. Other arrangements of external and implanted components can occur, as will be described later.

In the representative implementation shown in FIG. 2, a system 24 supports multiple prosthetic or therapeutic objectives. For purpose of illustration, in FIG. 2, the system 24 is capable of achieving (i) a hand-grasp function in upper extremity arm muscles; (ii) a standing function in lower extremity leg muscles; and (iii) a bladder and bowel control function.

To accomplish the different hand-grasp, standing, and bladder and bowel control functions, the system 24 dedicates, for each function, a function-specific external control signal source 12(1)(2)(3), a function-specific external pulse transmitter 16(1)(2)(3), a function-specific implanted receiver/stimulator 18(1)(2)(3), function-specific implanted leads 20(1)(2)(3), and function-specific implanted electrodes 22(1)(2)(3). To control all three function-specific receiver/stimulators, the system 24 employs a single, external pulse controller 26, which, for this reason, will also be called the "universal external controller." In concert with the other function-specific components, the universal external controller 26 selectively achieves all three hand-grasp, standing, and bladder and bowel control functions.

A. The Function-Specific Hand-Grasp Function Components

For the hand-grasp function, epimysial and intramuscular electrodes 22(1) are appropriately implanted by a surgeon in the patient's arm. The function-specific implanted electrodes 22(1) are positioned by the surgeon by conventional surgical techniques to affect desired neuromuscular stimulation of the muscles in the forearm and hand.

Desirably, the neuromuscular stimulation affected by the electrodes 22(1) achieves one or more desired palmar grasp patterns (finger tip-to-thumb pinching) and/or one or more desired lateral grasp patterns (thumb to flexed index finger pinching). The palmar grasp patterns allow the individual to grasp large objects (e.g., a cup or book), and the lateral grasp patterns allow the individual to grasp small or narrow objects (e.g., a pen or fork).

Implanted leads 20(1) connect the electrodes 22(1) to the function-specific implanted receiver/stimulator 18(1) in conventional ways. The receiver/stimulator 18(1) is placed by a surgeon under the skin on the chest. The receiver/stimulator 18(1) receives the stimulus timing and command signals and power from the universal external controller 26 through the function-specific external pulse transmitter 16(1).

In the illustrated embodiment, the pulse transmitter 16(1) takes the form of a transmitting coil, which is secured to a skin surface over the receiver/stimulator 18(1), e.g., by tape. The pulse transmitter 16(1) transmits the stimulus timing and command signals and power through the skin to the receiver/stimulator 18(1) for the hand-grasp function in the form of radio frequency carrier waves. The electrodes store electrical energy from the carrier waves. The stimulus timing and command signals for the standing function are distributed as biphasic current pulses in discrete channels to individual implanted electrodes 22(1). The biphasic pulses provide amplitude and duration electrical signals that achieve the desired coordinated muscular finger-grasp function. Because the implanted receiver/stimulator 18(1) receives power from universal external controller 26 through the external pulse transmitter 16(1), the implanted receiver/stimulator 18(1) requires no dedicated battery power source, and therefore has no finite lifetime.

The external control source 12(1) for the hand-grasp function is coupled to the universal external controller 26. As will be described in greater detail later, the external controller 26 can support a variety of external control sources 12(1), which can be coupled to the controller by cable or by wireless link, as will also be described in greater detail later.

In the embodiment illustrated in FIG. 1, the external controller 12(1) comprises a mechanical joy stick-type control device, which senses movement of a body region, e.g., the shoulder, which is therefore also called a shoulder position sensor. The shoulder position sensor can comprise, e.g., a two axis angle transducer that measures motion of the shoulder relative to the chest. The shoulder position sensor can be secured to the skin of the shoulder in the region of the sternal notch and clavicle using tape. As will be described later, when the user manipulating the shoulder in predetermined ways, the shoulder position sensor generates functional or proportional signals that, when processed according to the pre-programmed rules of the controller 26, select or deselect either palmar or lateral grasp patterns, proportionately control of the opening and closing of the hand, or lock the hand in a desired grasping position. As will be described in greater detail later, in an alternative implementation, manipulation of input buttons on the universal external controller 26 also can be used to perform these finger-grasp functions.

Further details of these function-specific components for the hand-grasp function can be found in Peckham et al U.S. Pat. No. 5,167,229, which is incorporated herein by reference. Commercial examples of such function-specific components can also be found in the FREEHAND™ System, sold by NeuroControl Corporation (Cleveland, Ohio).

B. The Function-Specific Standing Function Components

For the standing function, epimysial and intramuscular electrodes 22(2) are appropriately implanted by a surgeon in the patient's upper leg. The function-specific implanted electrodes 22(2) are positioned by the surgeon by conventional surgical techniques to affect desired neuromuscular stimulation of the muscles in the hip and thigh.

Desirably, the neuromuscular stimulation affected by the electrodes 22(2) achieves a contraction of leg muscles in the hip and thigh to bring the individual to an upright and standing position. In this position, the individual can stand upright and move about, typically with the aid of a walker or arm crutches.

Implanted leads 20(2) connect the electrodes 22(2) to the function-specific implanted receiver/stimulator 18(2) in conventional ways. The receiver/stimulator 18(2) is placed by a surgeon under the skin in the abdomen or thigh. The receiver/stimulator 18(2) receives the stimulus timing and command signals and power from the universal external controller 26 through the function-specific external pulse transmitter 16(2).

As in the finger-grasp function, in the illustrated embodiment, the pulse transmitter 16(2) for the standing function takes the form of a transmitting coil, which is secured to a skin surface over the receiver/stimulator 18(2), e.g., by tape. The pulse transmitter 16(2) transmits the stimulus timing and command signals and power through the skin to the receiver/stimulator 18(2) for the standing function in the form of radio frequency waves. As in the finger-grasp function, the stimulus timing and command signals for the standing function are distributed by the receiver/stimulator 18(2) in discrete channels to individual implanted electrodes 22(2) and provide electrical amplitude, duration, and interval command signals that achieve the desired coordinated muscular standing function.

The external control source 12(2) for the standing function is coupled to the universal external controller 26. As explained earlier in the context of the finger-grasp function, the universal external controller 26 can accommodate input from a variety of other external control sources, either by hard-wire or wireless links. In the illustrated implementation, the external control source 12(2) comprises a remote control button accessible to the individual, by which the user (or care giver) can select or deselect the standing function. One or more input buttons on the universal external controller 26 itself can also be used to select and deselect the standing function.

C. The Function-Specific Bladder and Bowel Control Function Components

For the bladder control function, cuff electrodes 22(3) are appropriately implanted by a surgeon about sacral nerves that lead to the bladder and bowel. The function-specific implanted electrodes are positioned by the surgeon by conventional surgical techniques to affect neuromuscular stimulation of muscles in the bladder, bowel and urethral sphincter.

Desirably, the neuromuscular stimulation affected by the electrodes 22(3) achieves a contraction of the muscles of the bladder, urethral sphincter, and bowel. After the bladder has contracted in response to the neuromuscular stimulation, it is possible to relax the sphincter muscles, allowing the bladder to empty.

Implanted leads 20(3) connect the electrodes 22(3) to the implanted receiver/stimulator 18(3) in conventional ways. The receiver/stimulator 18(3) is placed by a surgeon under the skin in the abdomen. The receiver/stimulator 18(3) receives the stimulus command signals from the universal external controller 26 through the external pulse transmitter 16(3).

As with the finger-grasp and standing functions, in the illustrated embodiment, the pulse transmitter 16(3) takes the form of a transmitting coil, which is secured to a skin surface over the receiver/stimulator 18(3), e.g., by tape. The pulse transmitter transmits the stimulus command signals through the skin to the receiver/stimulator 18(3) for the bladder and bowel control function in the form of radio frequency waves.

As explained earlier in the context of the finger-grasp and standing functions, the universal external controller 26 can accommodate input from a variety of other external control sources 12 (3), either by hard-wire or wireless links, to also affect the bladder and bowel control function. In the illustrated implementation, the external control source 12(3) for the bladder and bowel function comprises an external remote control device, that can select or deselect the bladder and bowel control function. One or more input buttons on the universal external controller 26 itself can also be used to select and deselect the bladder and bowel control function.

Further details of these function-specific components for the bladder and bowel control function can be found in Brindley U.S. Pat. No. 3,870,051, which is incorporated herein by reference. Commercial examples of such function-specific components can also be found in the VOCARE™ System, sold by NeuroControl Corporation (Cleveland, Ohio).

D. The Universal External Controller

As FIGS. 3A, 3B, 3C, and 4 show, the universal external controller 26 is desirably housed in a compact, lightweight, hand held housing 28. In one implementation, the housing 28 measures about 9.5 cm by 5.6 cm×2.7 cm, and weighs, e.g., about 160 g. As such, the controller 26 readily fits into a pocket or can be clipped onto the belt of an individual.

Desirably, the controller 26 is battery powered. In the illustrated embodiment, the controller 26 includes a power input slot that receives an interchangeable, rechargeable, industry-standard battery 30 (see FIG. 4), e.g., a Lithium Ion battery used in association with a MOTOROLA™ Star Tech™ Cellular Phone. The controller 26 desirably interchageably accommodates rechargeable batteries of various capacities, so that different power usage levels of the controller (depending upon the number and type of prosthetic functions of the controller 26) can be readily supported.

Desirably, the battery 30 cannot be charged when connected to the universal external controller 26, so that the controller 26 (and, thus, the user) cannot be connected to main power. Instead, the battery 30 must be removed and coupled to an associated external battery charger (not shown).

The controller 26 also desirably includes a display screen 32 and keypad 34, which together form an interactive interface between the individual user and the controller 26. The display 32 can comprise, e.g., a liquid crystal display. The display 32 presents to the individual pertinent operational and status information, and also prompts the individual to select or modify operational settings using the keypad 34. The keypad 34 can comprise, e.g., a one-piece silicone-rubber molded unit.

The controller 26 desirably houses a microprocessor 36, which, in the illustrated embodiment (see FIG. 4), is implemented on a main, double-sided circuit board 38. The main circuit board 38 carries the components of the microprocessor 36, e.g., high and low voltage supplies, a high voltage protector, input/output ports 112 (shown in FIG. 3B) and drivers for the external control signal sources and pulse transmitters, a microcontroller, keypad interface, the liquid crystal display 32, and an audio device (e.g., a buzzer). The microprocessor 36 also desirably includes a 900 MHz transceiver, to allow wireless linking between the controller 26 and a compatible external wireless control signal source 12(1)(2)(3), as will be described in greater detail later. If desired, additional full size or half-size circuit boards 40 (see FIG. 4) can be optionally provided, to handle special input signal conditioning for one or more of the function-specific control signal sources (e.g., the joy stick-type shoulder position sensor).

The microprocessor 36 can be realized with, e.g., a conventional MC68HC12 microcontroller. The microprocessor 36 also desirably includes a flash memory device on the main circuit board 38, which can be realized with e.g., a conventional EEPROM memory chip. The flash memory device carries embedded, programmable code, which will also be call the "firmware." The firmware expresses the pre-programmed rules or algorithms under which the stimulation timing and command signals are generated in response to input from the various external control sources, as well as the pre-programmed rules or algorithms that govern operation of the display 32 and keypad 34 of the controller 26 to create the user interface, as well as the other input/output devices supported by the controller 26.

The microprocessor 36 of the controller also desirably includes an infrared transceiver. The transceiver allows the wireless transfer of information to and from the microprocessor through an optical lens 42 (see FIGS. 3C and 4). This makes possible wireless programming of the firmware by infrared link by an external computer, as will be described later. This also makes possible wireless linking between two or more controllers 26, for exchange of information and for replacement and backup purposes. As will be described later, the microprocessor 36 also accepts programming input via the input keypad 34, allowing the individual user or care giver to program operation of the controller 26 to the extent permitted by the firmware.

In the illustrated embodiment, the housing 28 encloses the display 32, keypad 34, and circuit board(s) 38 and 40 between front (keypad side) and rear (battery side) housing shells 44 and 46, which can be made, e.g., from molded ABS impact-resistant plastic. Spash-proof gaskets 48 are desirably placed at appropriate places, e.g., about the keypad, battery contacts, and housing shells, to seal the housing 28 against ingress of moisture. A LCD lens window 50 desirably covers the display 32. Pivots 52 for a conventional flip cover can also be provided on the housing 28.

1. Main Circuit Board Components

FIG. 5 shows a representative circuit block diagram for the microprocessor 36 of the universal external controller 26. The specific circuitry shown in FIG. 5 allows the selection of a desired neuromuscular stimulation objective and supports the generation of output signals to one neuromuscular stimulation assembly to achieve the objective. However, it should be appreciated that the circuitry can be modified to include multiple parallel output stages, so that concurrent outputs to different neuromuscular stimulation assemblies can be provided.

As shown in FIG. 5, the circuitry is built on two printed circuit boards: the main circuit board 38 and the auxiliary board 40. FIGS. 5A to 5M show representative circuit schematics for the components carried on the two boards 38 and 40.

The main circuit board 38 consists of five circuit modules. These are (see FIG. 5) the power supply module 200, the implant driver module 202, the microcontroller module 204, and the user interface module 206. The representative implementation mounts these modules on a double-sided, 6-layer FR4 printed wiring main circuit board 38 (88 mm×49 mm).

In the illustrated embodiment, the functions supported by the main circuit board 38 include: (i) mounting of push buttons of the keypad 34 for user control; (ii) mounting of the display 32 and audio device for user prompting and information display; (iii) mounting of contacts for user serviceable battery 30; (iv) mounting of output plug contacts for the indicated function-specific pulse transmitters; (v) an interface to auxiliary control boards 40, e.g., for specialized function-specific control signal sources 12(1) (2) (3); (vi) control of processing functions via the microprocessor 36 and memory chip; (vii) interface to the keypad 34, display 32, audio device, and other user interfaces to the microprocessor 36; (viii) drivers for the indicated function-specific pulse transmitters 16(1)(2)(3); (ix) interface to the battery 30, including detection of battery charge status; (x) provision of an infrared communications link; and (xi) provision of a 900 MHz communications link.

Various circuit components and configurations can be placed on the main board to realize these and other functions. A representative implementation will be generally described with reference to FIGS. 5A to 5M and associated tables. The representative implementation meets medical grade IPC standard design rules, using no wires and all standard components, except one custom made transformer. The representative implementation uses no adjustable components, except one trim capacitor (to accommodate variations in the one custom made transformer). The representative implementation is EMC compatible.

The Power Supply Module 200 includes a low-voltage supply circuit 208 (shown schematically in FIG. 5A) and a high-voltage supply circuit 210 (shown schematically in FIG. 5B). The low-voltage supply circuit 208 converts the battery voltage of 2.7 to 4.2 V to the general circuit operation voltage of 5.0 V. The high-voltage supply circuit 212 converts the same battery voltage to the variable operating voltage for the implant drivers (5.0 to 8.5 V for the finger-grasp and standing functions, and 10 to 40 V for the bladder/bowel control function). Each voltage supply circuit 208 and 210 is a DC/DC converter built around a specific IC chip. The level of the high voltage is set by the microcontroller module 204 via a DAC. A high-side current sensing IC provides output current value to the microcontroller module 204.

The Implant Driver Module 202 includes the function-specific driver 212 for the bladder and bowel control function (FIG. 5D), the function-specific driver 214 for the hand-grasp function (FIG. 5E), and the function-specific driver 216 for the standing function (FIG. 5F), with an associated high voltage protector (FIG. 5C), to provide failsafe hardware protection. The hand-grasp and standing function drivers 214 and 216 generate amplitude-modulated carrier of 6.78 MHz for powering and communicating with the implanted function-specific receivers/stimulators, respectively 18(1) and 18(2). As will be described in greater detail later, the output RF for each of these drivers 214 and 216 can be set by the user at one of five levels between 0.5 to 1.0 W. This variable RF power setting ensures reliable coupling to the associated implanted function-specific receiver/stimulator 18(1) or 18(2) at the specific depth of implantation (which can vary), while minimizing battery consumption. The bladder and bowel control driver 212 generates high voltage (10 to 40 V), high current (up to 1 A) pulses to excite the associated receiver/stimulator 18(3). Three identical output stages can be controlled by the microcontroller module 204 for interfacing with either a 3-channel or a 2-channel receiver/stimulator 18(3). The function of the high-voltage protector 218 is to prevent accidental application of high voltage to the finger-grasp or standing drivers 214 to 216 in case of a firmware failure.

The Microcontroller Module 204 (schematically shown in FIG. 5G) is built around a Motorola HC12 chip. The HC12 chip has 1-kbyte RAM and 32-kbyte flash EEROM. The built-in flash memory is used for the system firmware. An external 8-kbyte EEPROM chip is used for user-specific data, such as for finger-grasp patterns (as will be described later). A 4-MHz ceramic resonator is selected for obtaining a 2-MHz clock frequency in the HC12. The HC12 uses a synchronous serial peripheral interface (SPI) to communicate with three peripheral chips: the LCD display driver; the DAC for high-voltage setting; and the ADC in the auxiliary board 40 (as will be described later. The HC12 also uses an asynchronous serial communication interface (SCI) to communicate with the infrared transceiver 220 (shown schematically in FIG. 5K) and the 900-MHz transceiver 222 (shown schematically in FIG. 5L). The internal 8-channel, 10-bit ADC of the HC12 is used to monitor the critical parameters such as battery voltage, output voltage to the low-voltage supply 208, output voltage and output current of the high-voltage supply 210, and the received signal strength of the 900-MHz transceiver 222.

Figure 5A:
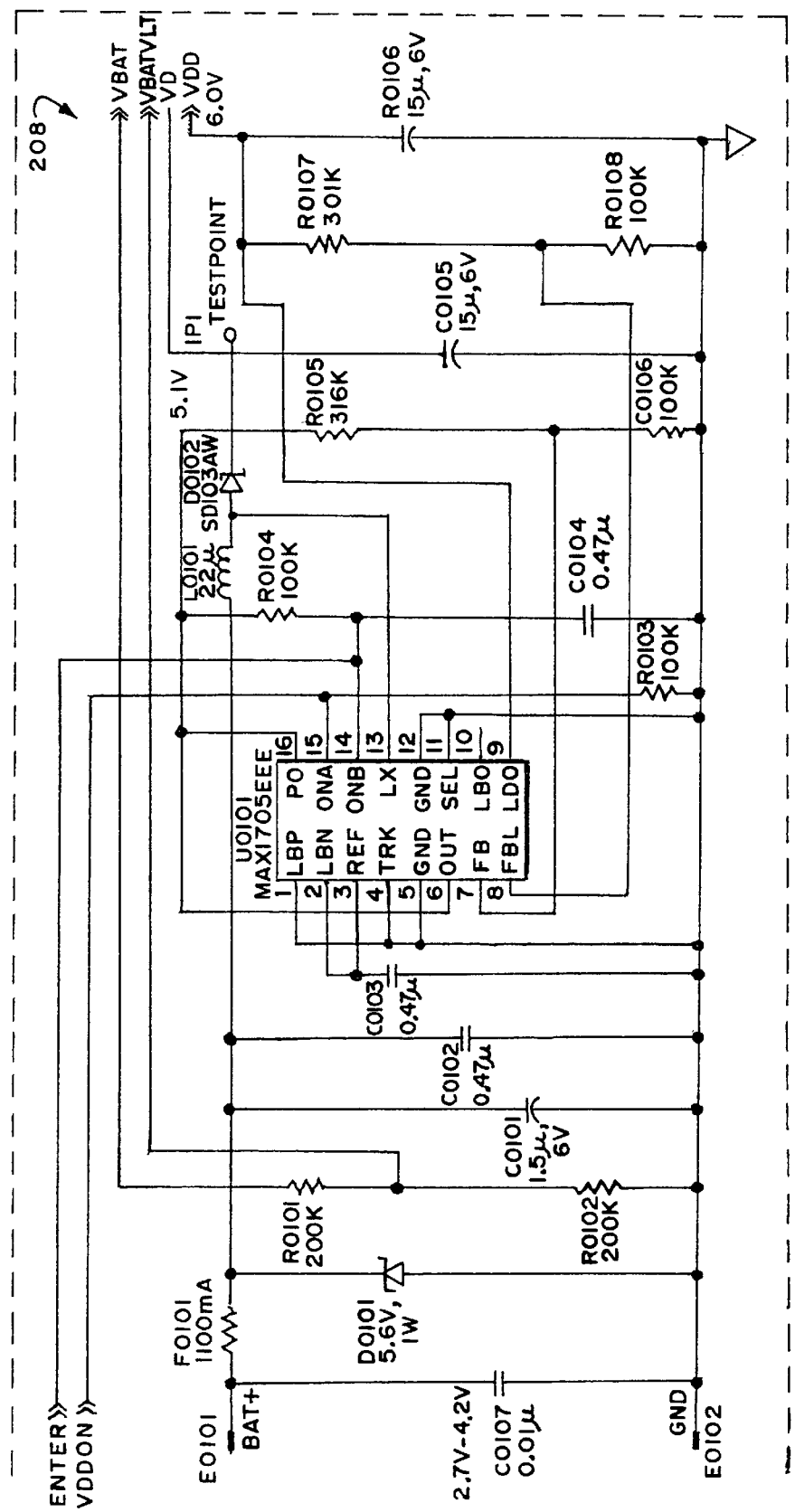
Figures 1, 5B:
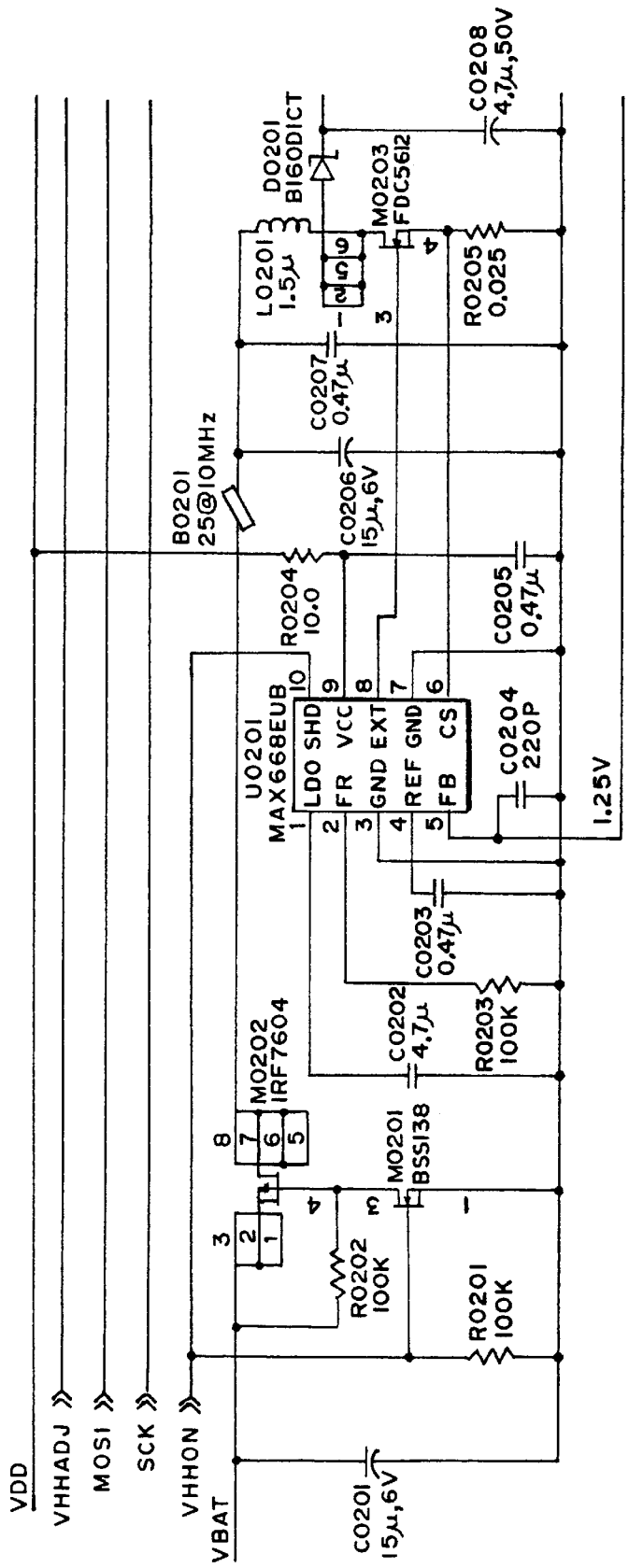
Figures 2, 5B:
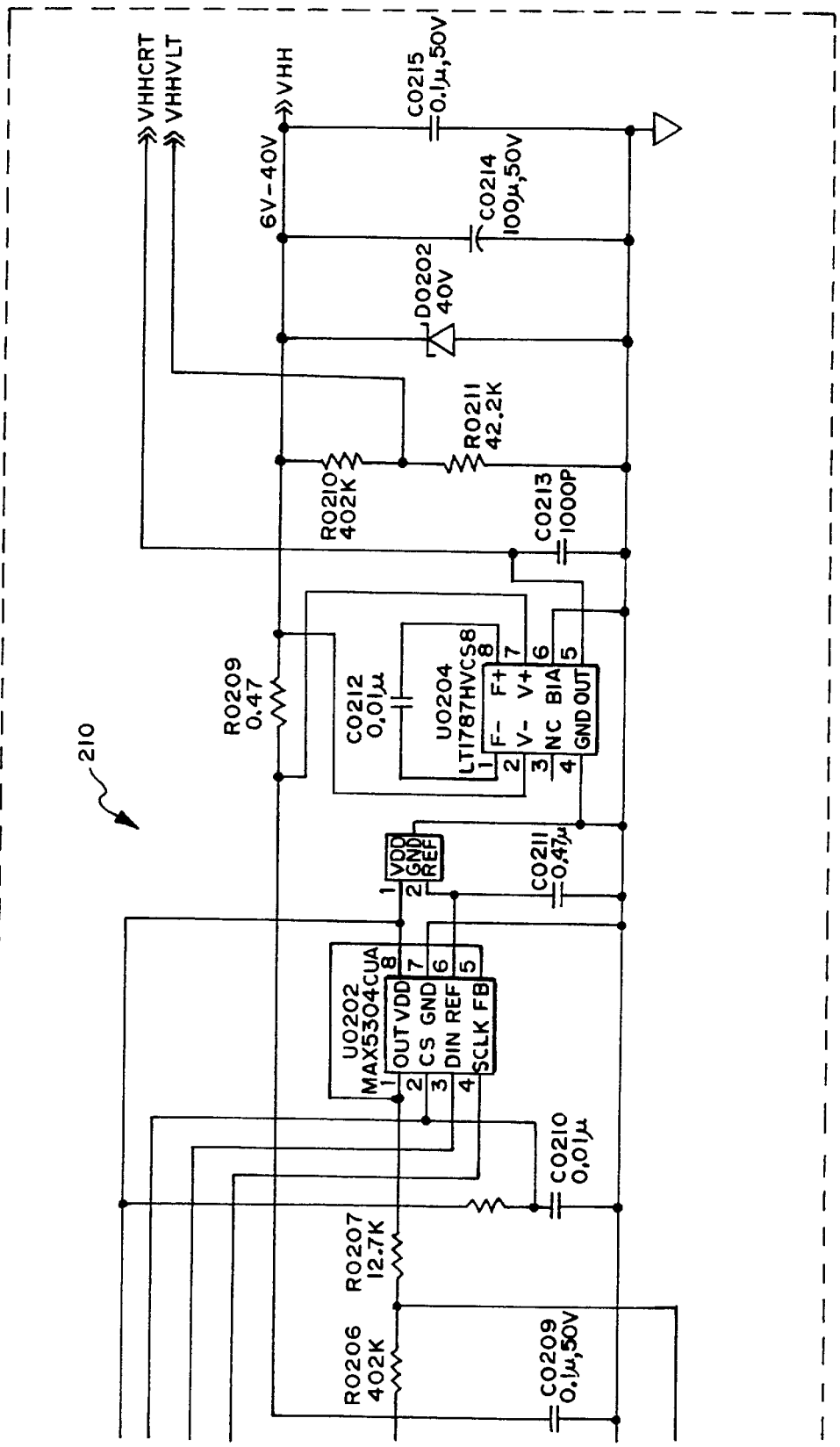
Figure 5C:
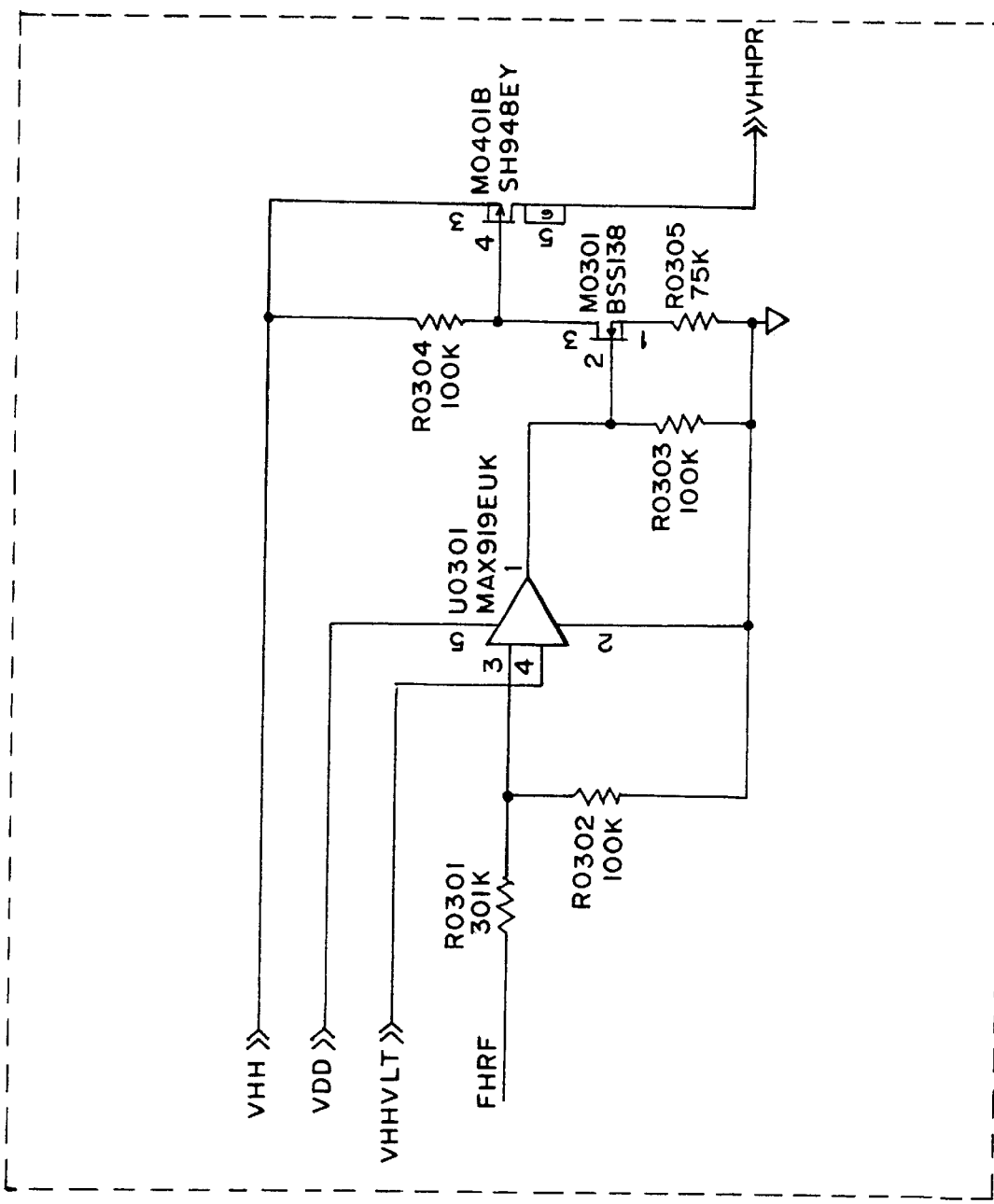
Figure 5D:
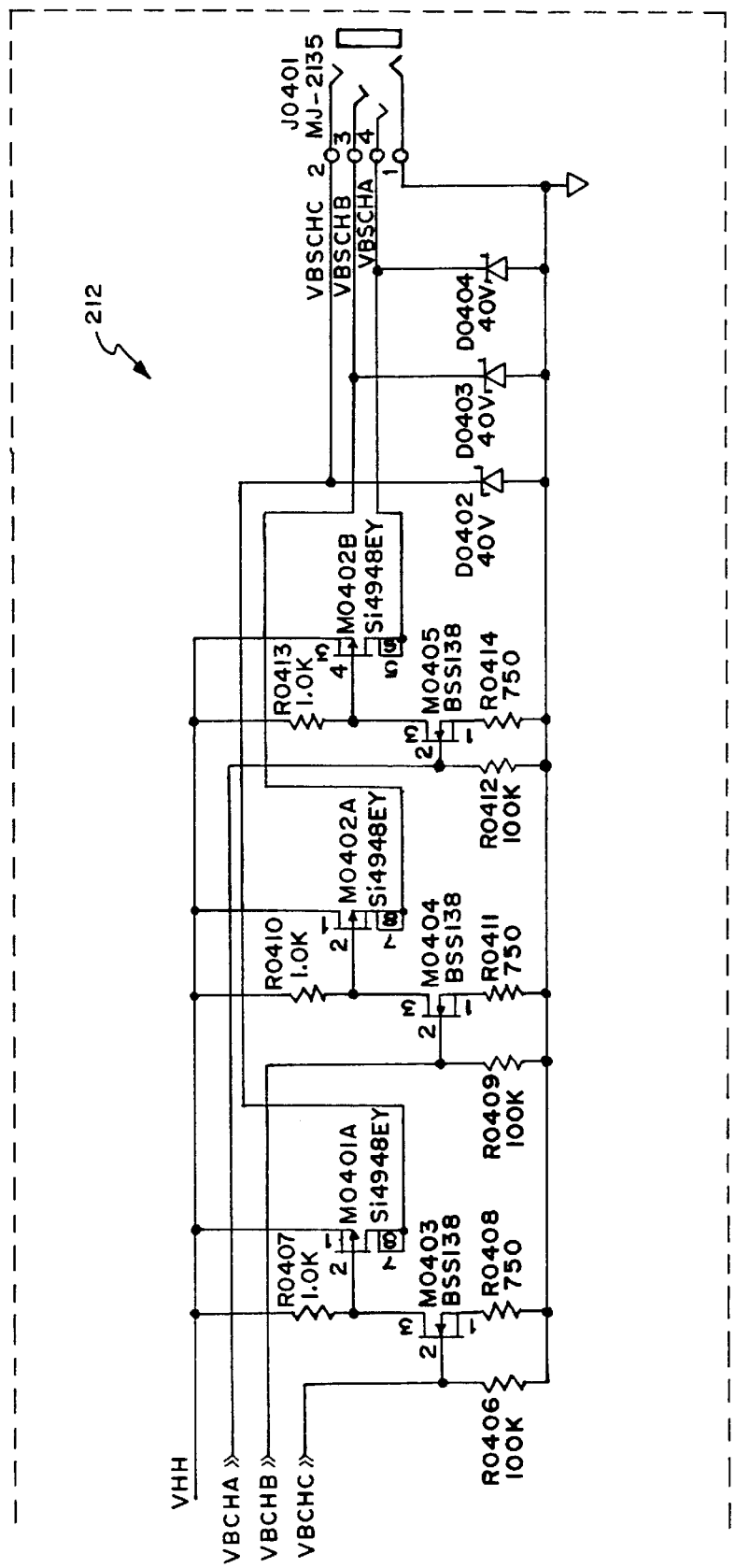
Figures 1, 5E:
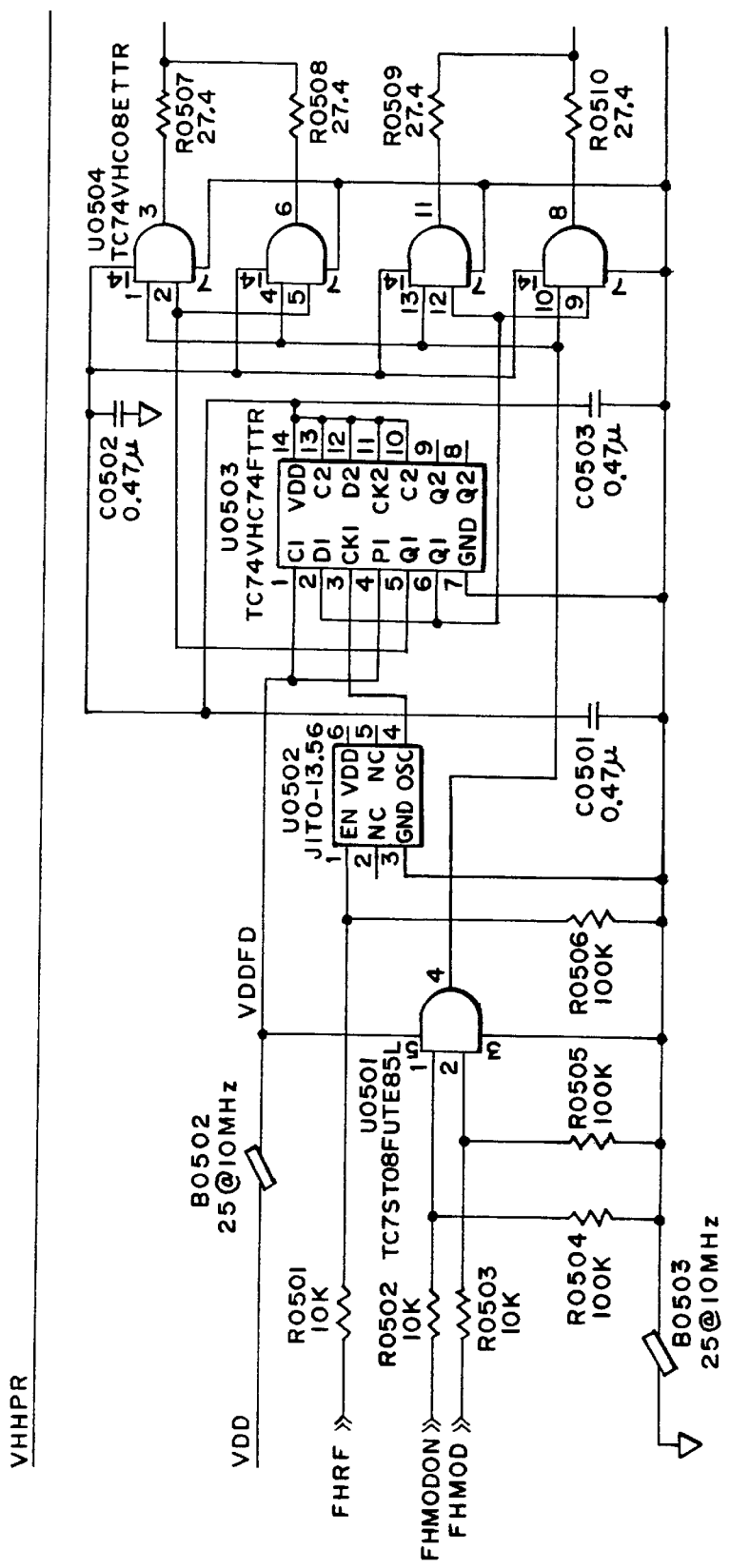
Figures 2, 5E:
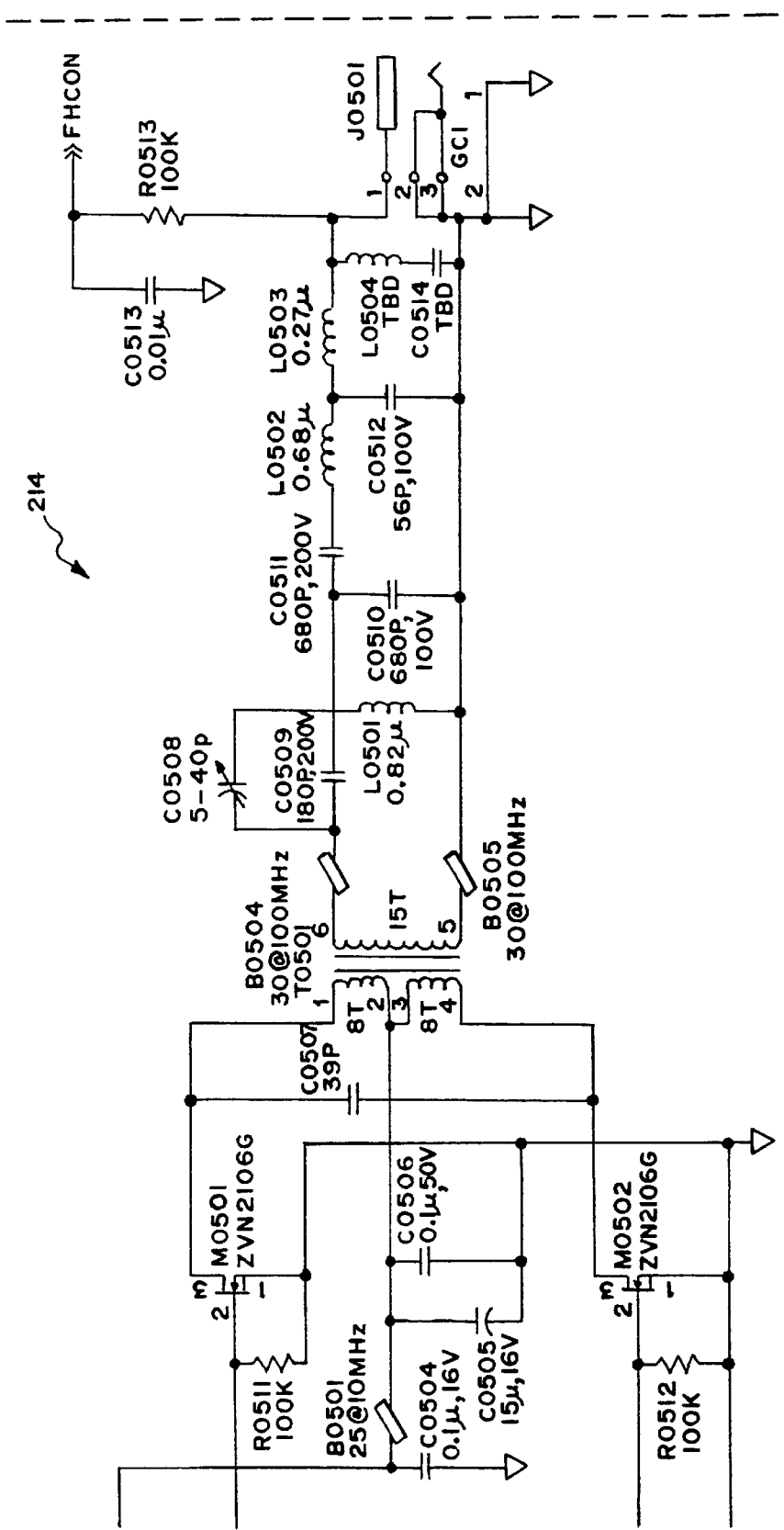
Figures 1, 5F:
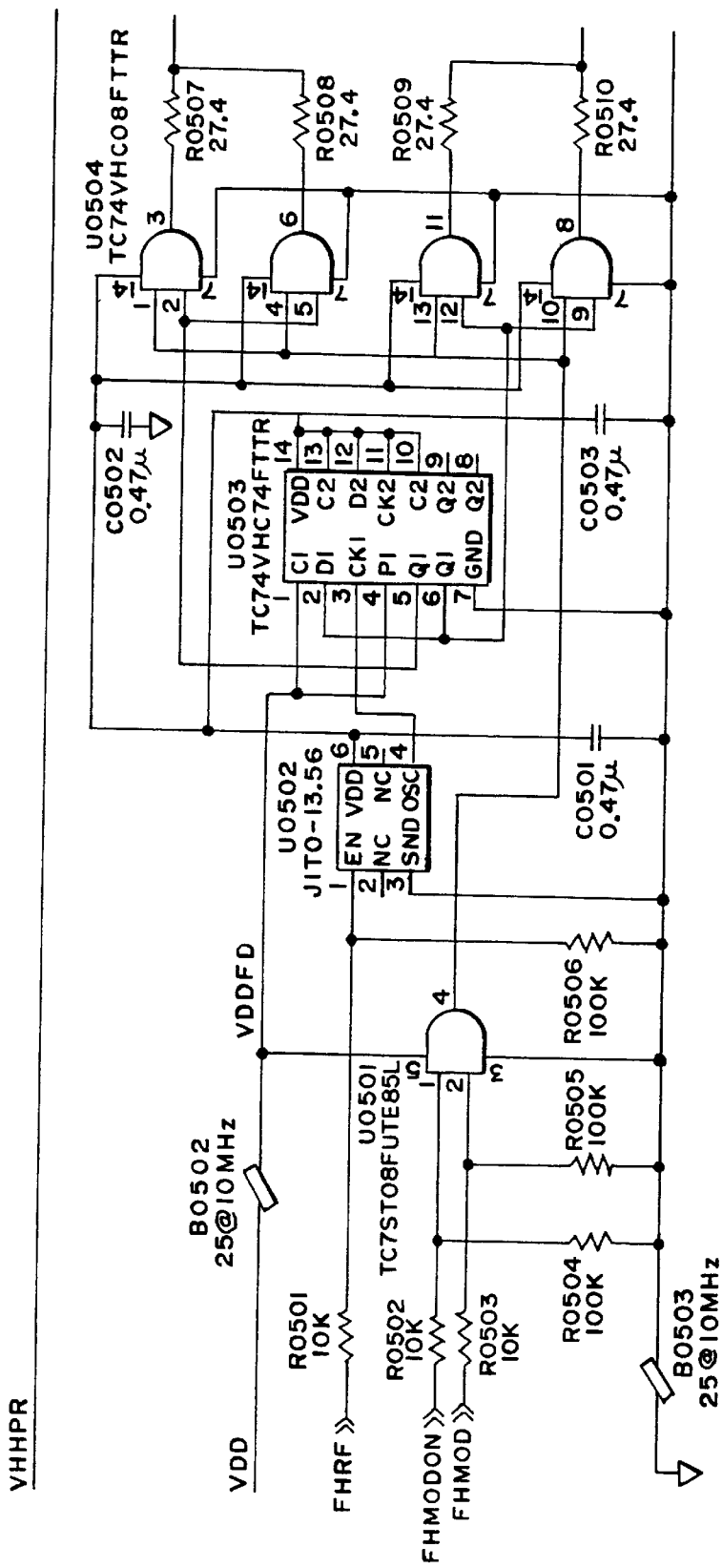
Figures 2, 5F:
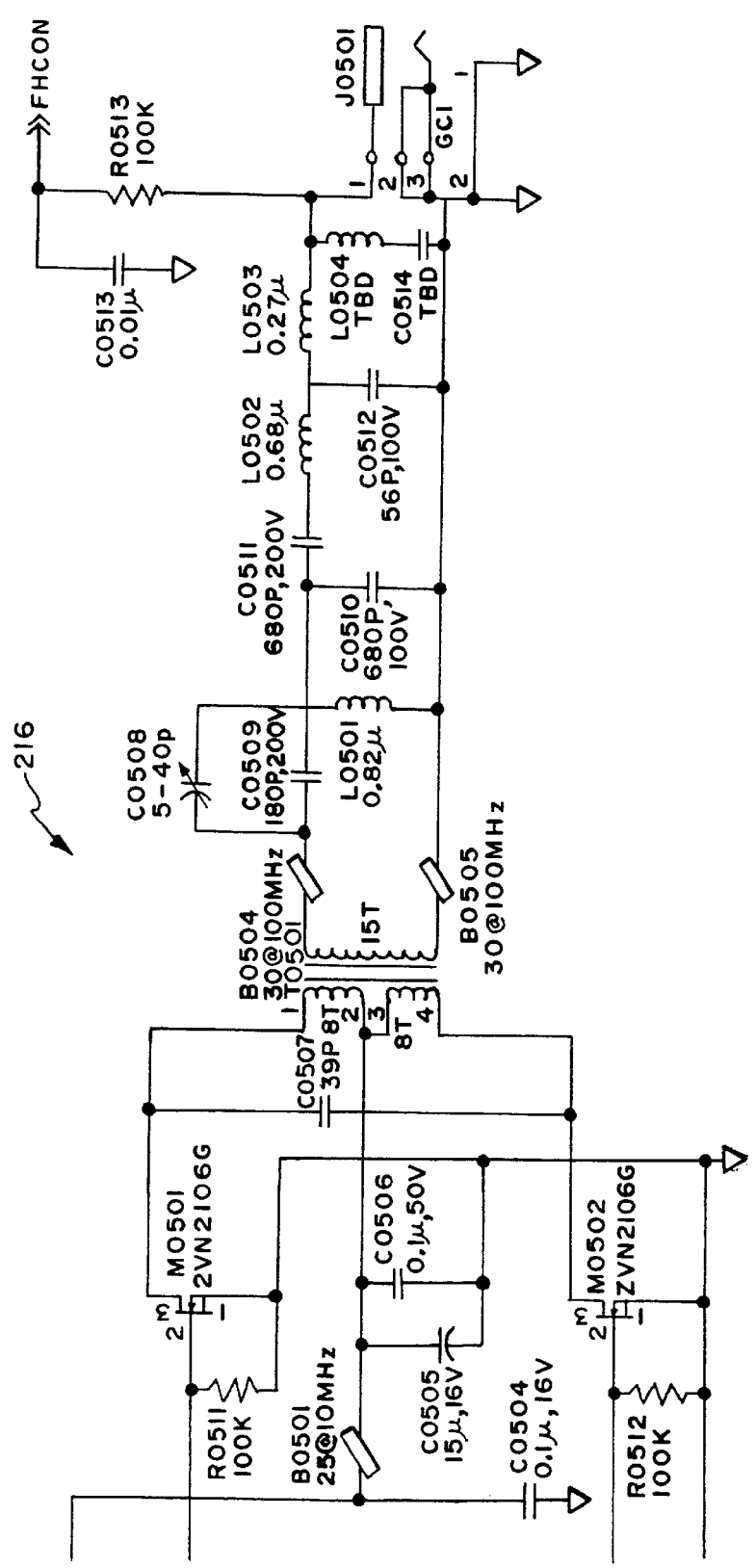
Figures 1, 5G:
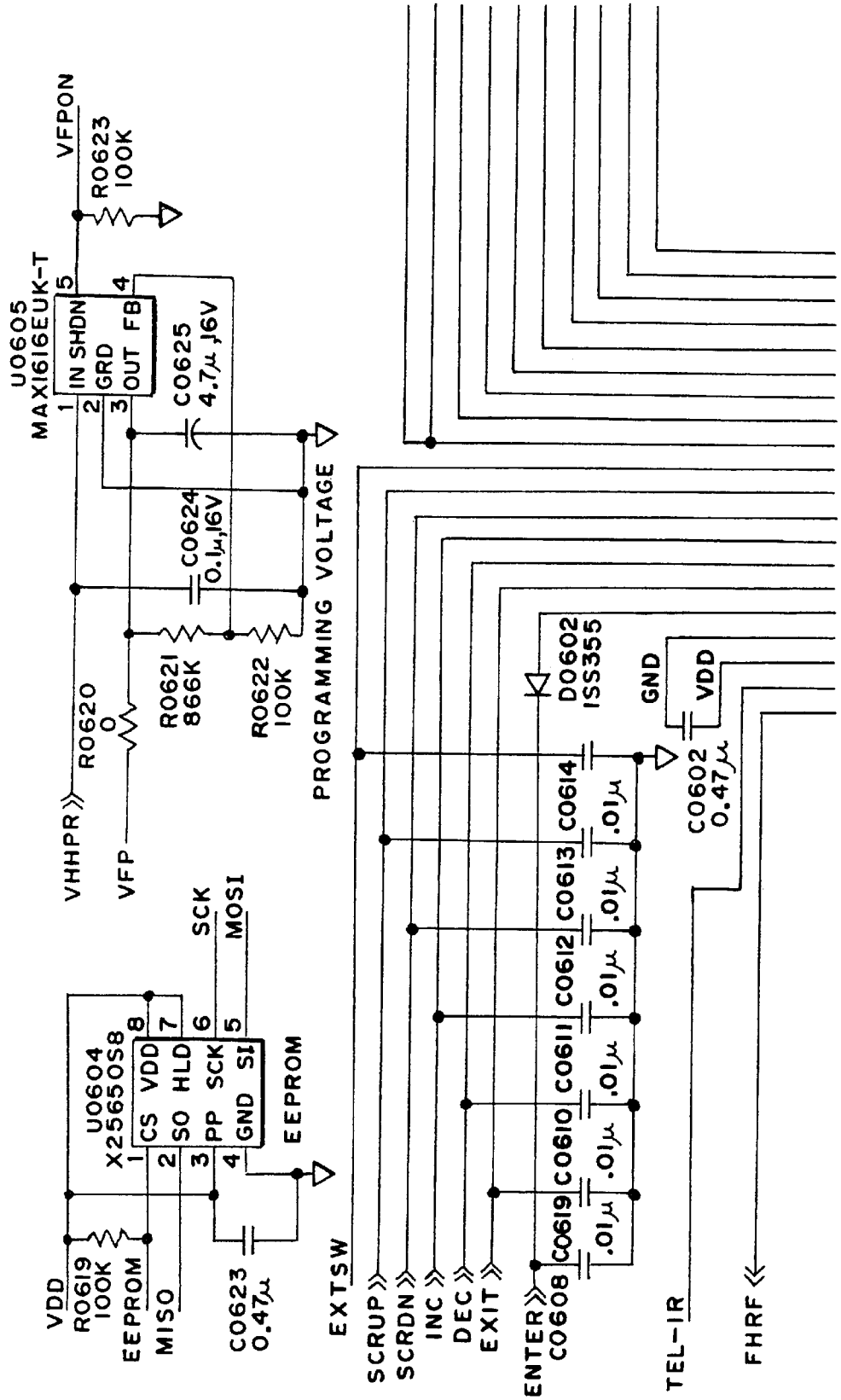
Figures 2, 5G:
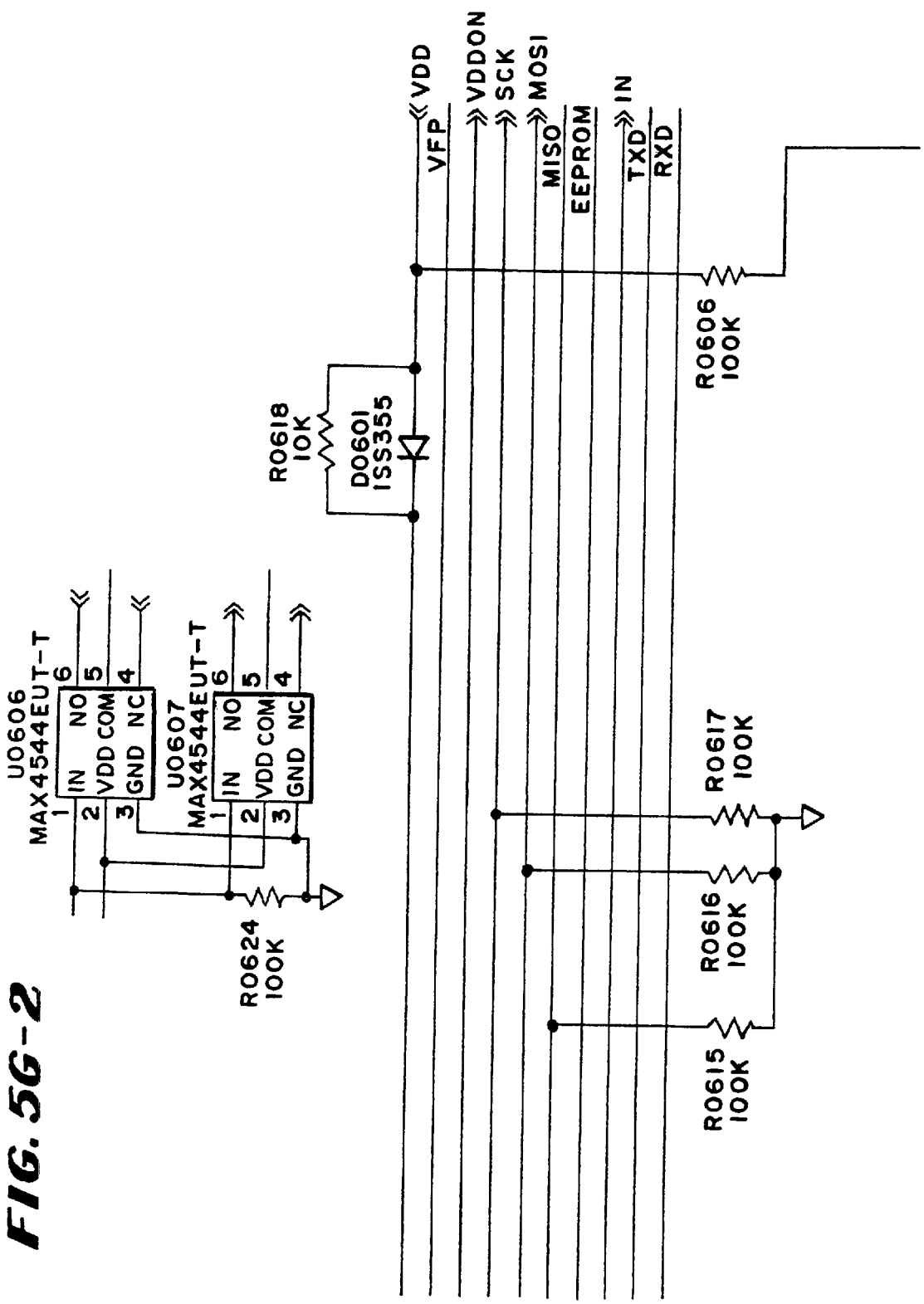
Figures 3, 5G:
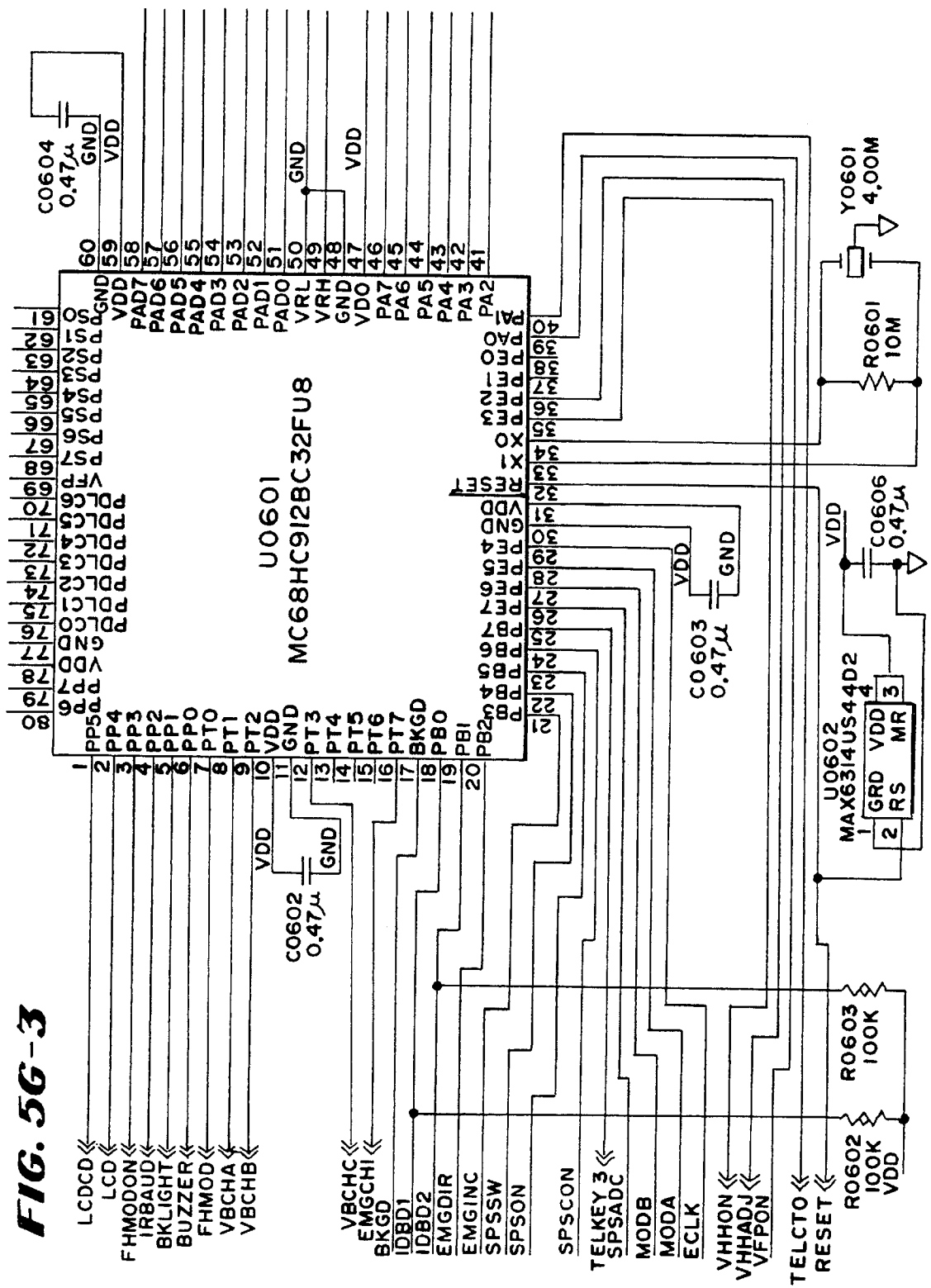
Figures 4, 5G:
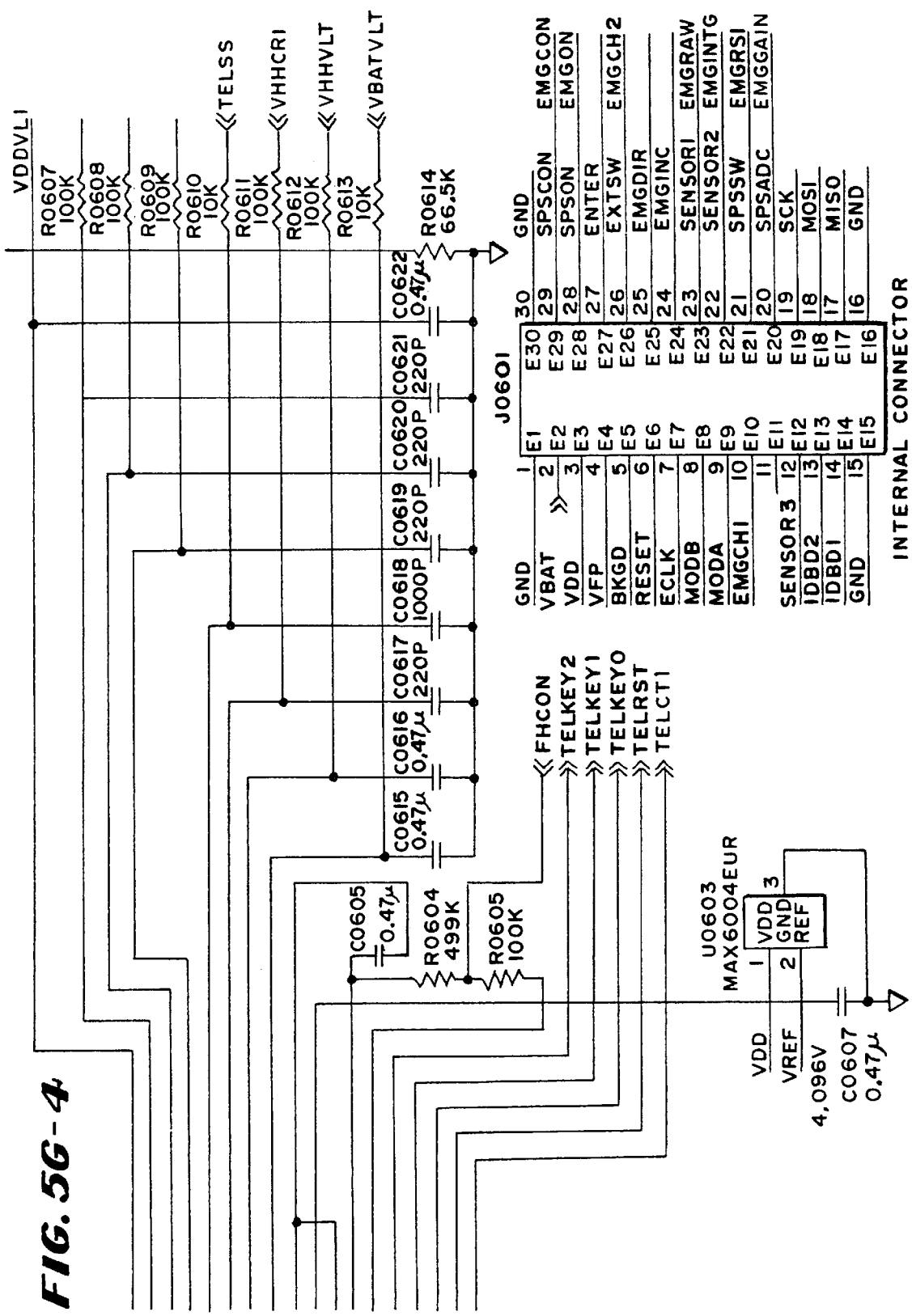
Figures 5H, 5I:
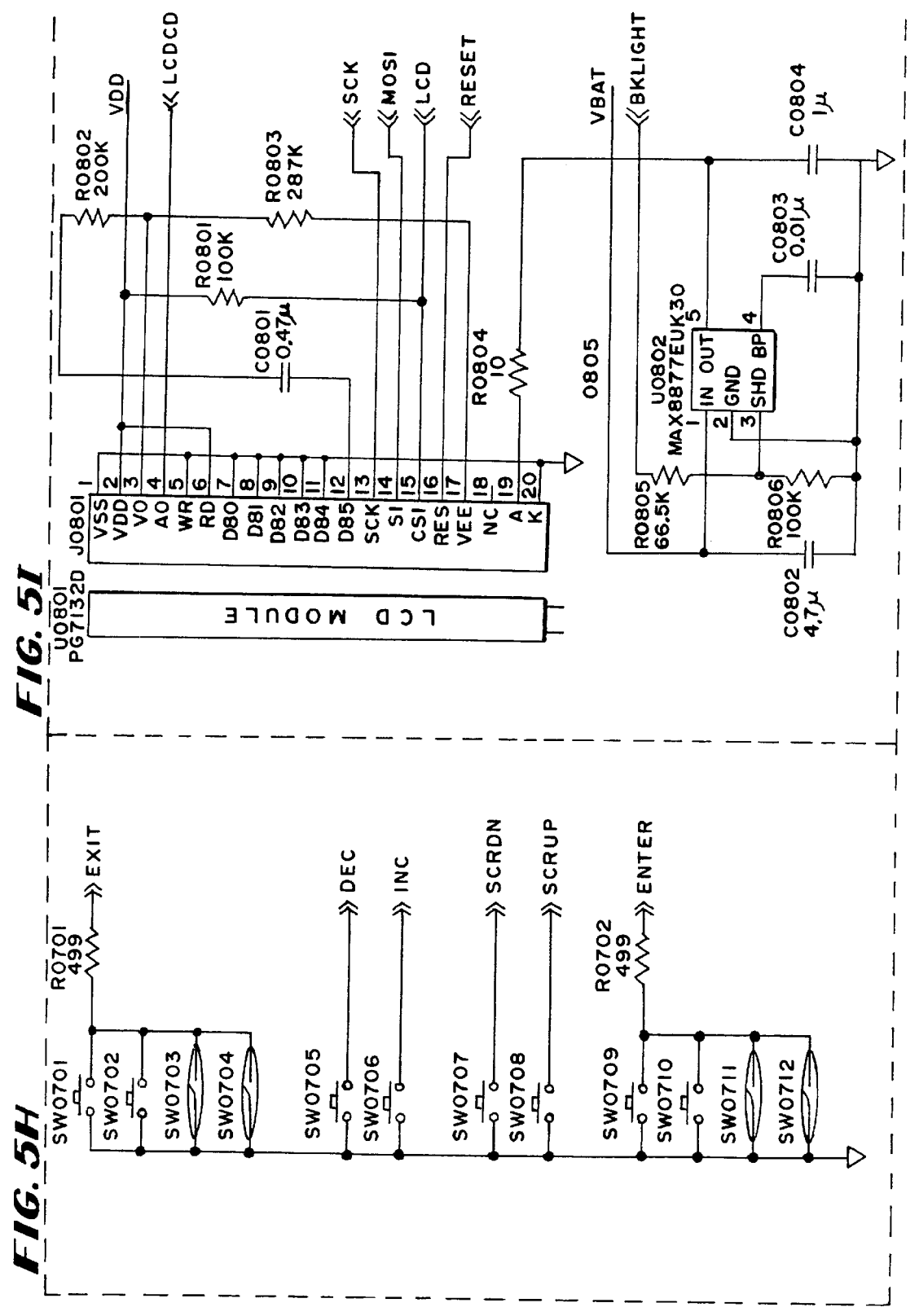
Figures 1, 5L:
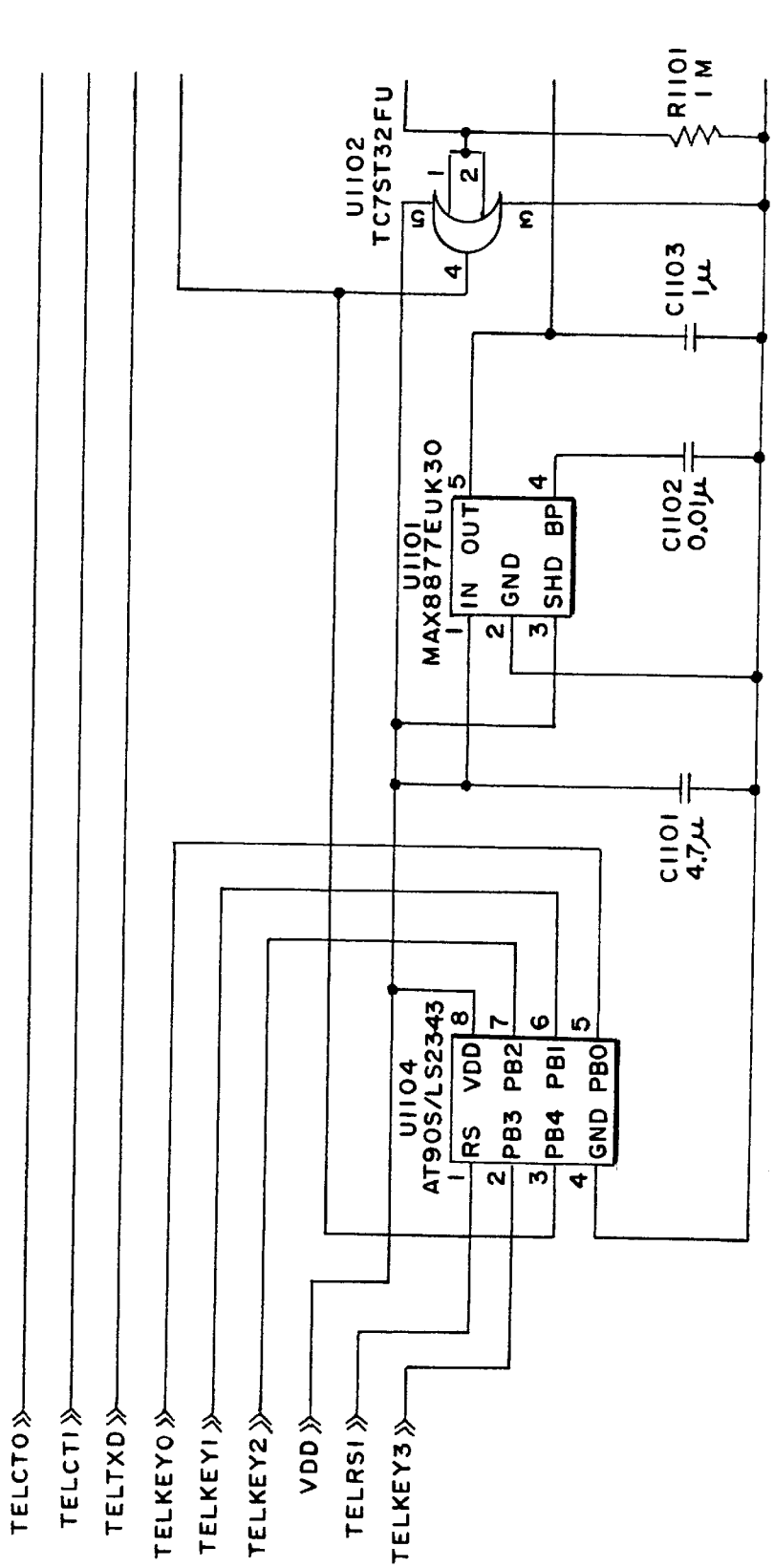
Figures 2, 5L:
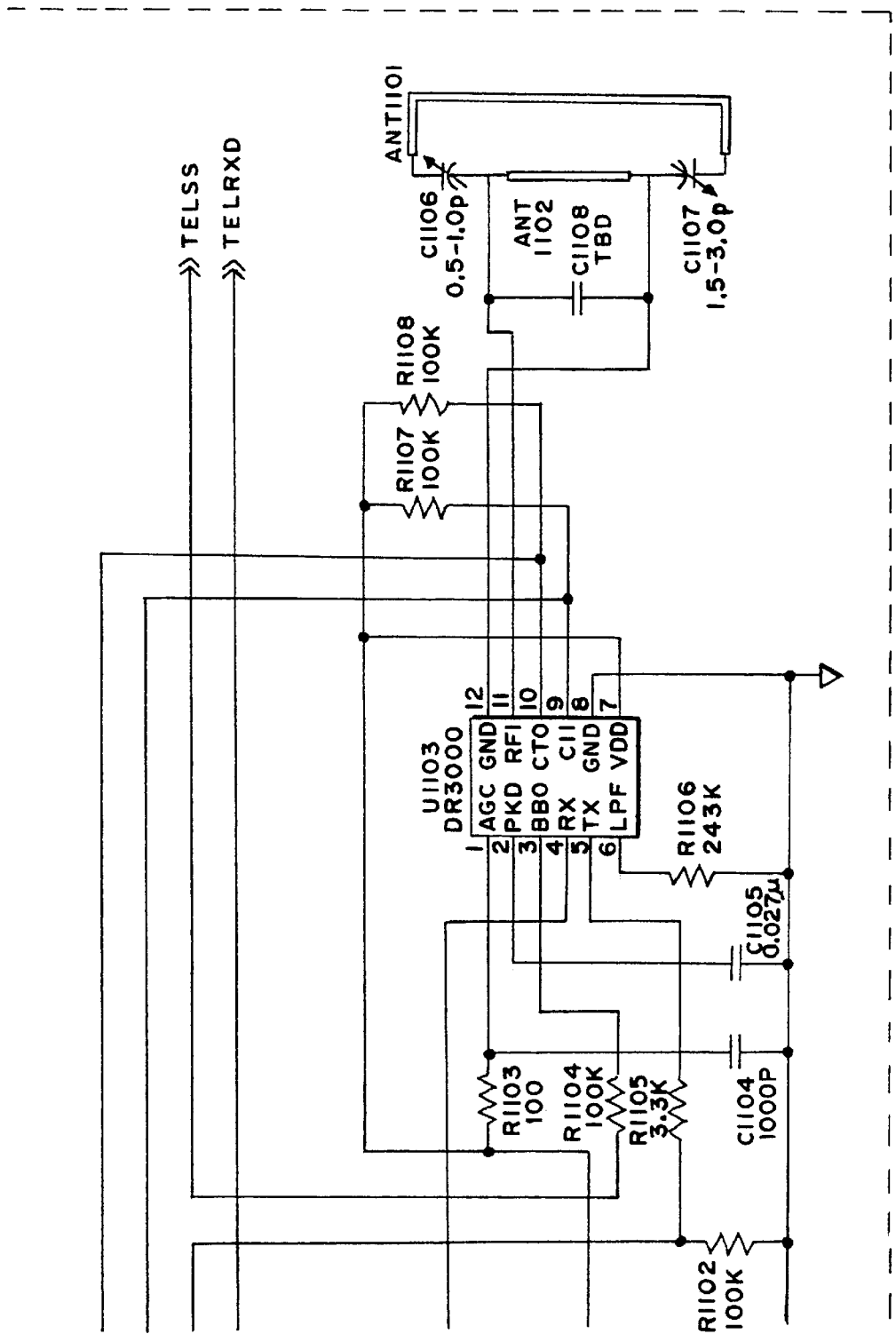

The User Interface Module 206 consists of the circuitry 224 for the keypad 34 (shown schematically in FIG. 5H), the circuitry 226 for the liquid crystal display (LCD) 32 (shown schematically in FIG. 5I), and the circuitry 222 for the 900-MHz transceiver (shown in FIG. 5L). In the keypad circuit 224, a pair of perpendicularly situated reed switches is connected in parallel to each of the regular pushbutton switches for the "enter" and "exit" functions, as will be described later. The reed switches allow the user to operate the device using a finger ring with a magnet, without having to physically touch the keypad 34. The LCD circuit 226 has a 16 character×4 roll screen 32 with LED back lighting. The volume of the sound generated by the buzzer circuit 228 (shown schematically in FIG. 5J) is adjustable by changing the pulse width. The infrared transceiver 220(shown schematically in FIG. 5K) is implemented with a transceiver IC and discreet transmitting LED and receiving photo diode. The 900 MHz transceiver (shown schematically in FIG. 5L) is formed with a loop antenna, an amplitude-sequenced hybrid (ASH) transceiver module, and a dedicated microcontroller chip for decoding the received commands. Input and output level shifters are used for interfacing the 3-V transceiver module 222 with the 5-V HC12 microcontroller.

In the representative implementation, the controller also includes a double-sided, 6-layer FR4 printed wiring board 40 (40 mm×46 mm) (shown schematically in FIG. 5M), which serves as an input signal conditioning card for a joy-stick type shoulder position sensor, which is used in the illustrated embodiment to carry out the finger-grasp function. The main board 38 and auxiliary board 40 are connected together through a 30-contact interboard connector 240. The auxiliary board 40 includes an input filter 230 having low-pass filters and surge suppressors for improving immunity to electromagnetic interference. The auxiliary board 40 also includes a differential amplifier 232, which has two instrumentation amplifier IC chips set a gain of 10 for both X and Y axis signals coming from the shoulder position sensor. The auxiliary board 40 also includes a an analog-to-digital converter 234, which is a 2-channel, 12-bit serial ADC chip. A power supply 236 on the board 40 uses a charge-pump IC to convert battery voltage to the 5 V excitation level for the shoulder position sensor. The 5 V output is pulsed at a duty cycle of $\frac{1}{16}$ to conserve battery power. The board 40 also includes switch interface relays 238, which relays the two external switches to the microcontroller module 204, while also providing the signal about the connection of the sensor or the switches.

The following tables describe for ready reference further details of the components and their functions as shown in FIGS. 5 and 5A to 5M.

TABLE 1

The Low Voltage Supply Circuit 208 (FIG. 5A)

| Component | Description | Circuit Function |
|---|---|---|
| F1101 | THERMAL SWITCH/FUSE 1.1 A | Limits magnitude and duration of over voltage clamped currents from battery input |
| D1101 | DIODE, ZENER 5.6 V | Protects LV Regulator and VDD powered devices (CPU) from static discharge and accidental over voltage |
| C1101, C1102 | Capacitors | Filter noise fed back to battery voltage network |
| R1101, R1102 | Resistors | Divider for CPU VBAT monitor input |
| U1101 | PWM DC/DC Power Up Converter | Provides control and power switching for Low Voltage Flyback power converter |
| C1103 | Capacitor | Filters switching noise within and to U1101 regulator |
| R1104, C1104 | R-C Network | Pull-Up (dissable) and flitch filter for PENTER/V$_{LV}$ ONB (active low) |
| R1103 | Resistor | Pull-Down (dissable) VDDON ONA (active high) |
| L1101 | Inductor, Power | Dynamic energy storage for power conversion |
| D1101 | Rectifier, Schottky 40 V, 400 mA | Switch mode communtating Rectifier |
| C1105 | Capacitor | Switching Output Filter |
| R1105, R1106 | Resistors | Low Voltage Switching Regulator feedback sense divider |
| R1107, R1108 | Resistors | Low Voltage Linear Regulator feedback sense divider |
| C1106 | Capacitor | Linear Output Filter |

TABLE 2

The High Voltage Supply Circuit 210 (FIG. 5B)

| Component | Description | Circuit Function |
|---|---|---|
| C2101 | Capacitor | Filter HV Converter noise fed back to battery voltage network |
| M2102 | Power MOS FET, P Ch | HV Converter battery power switch |
| M2101 | Power MOS FET, N Ch | Gate drivers for M2102 |
| R2101, R2102 | Resistors | Gate drivers networks for M2102 and M2102 |
| U2101 | PWM DC/DC Power Up Converter | Provides control and drive for High Voltage Flyback power converter |
| C2102–C2104 | Capacitors | Filters switching noise within and to U2102 regulator |
| R2103 | Resistor | Sets basic switching frequency for U2101 regulator |
| R2104, C2105 | R-C Network | Supply +5 V, (VDD) to U2101 and decouple VMOS gate drive noise from MPU supply |
| B2101, C2106, –7 | R-C Network | Supply VBAT to storage inductor L2101 and decouple power switching noise battery voltage network |
| L2101 | Inductor, Power | Dynamic energy storage for power conversion |
| M2103 | Power MOS FET, N Ch | Power converter switch |
| R2105 | Resistor, Low W | Current Sense, PWM control, limit |
| D2101 | Rectifier, Schottky 60 V, 1.0 A | Switch mode communtating Rectifier |
| C2108, C2109 | Capacitors | Switching Output Filter |
| R2106, R2107, U2102 | Resistors, Potentiometer, Digital 32 pos linear | High Voltage feedback sense divider with CPU control through setting or the digital Pot |
| R2108, C2110 | R-C Network | Power up preset network for U2102 |
| U2103 | Transconductance Current Sense Amp | Translates current sense voltage across pins 2–7 input to ground reference signal |
| R2109 | Resistor | Current sense Scaling Resistor |
| C2112 | Capacitor | Output noise filter |
| R2111–R2113 | Resistor Divider Net | Divides HV level for CPU HV monitor input and Free hand HV upper limit |

TABLE 3

The Bladder and Bowel Control Function Driver 212 (FIG. 5D)

| Component | Description | Circuit Function |
|---|---|---|
| D2201–D2204 | ZENER TRANSIENT CLAMP DIODE | Protects HV Power and VOCARE Switches from transient discharge and loss of HV converter control |
| C2201, C2302 | Capacitors | Filter HV Converter noise and provide energy reservoir for VOCARE pulse load |
| M2202B | Power MOS FET, P Ch | HV Converter switch for Free Hand Driver |
| M2202A, M2205A, B | Power MOS FET, P Ch | HV Converter switch for VOCARE Coils C, B, A |
| M2201, –3, –4, –6 | Power MOS FET, N Ch | Gate drivers for M2202 and M2205 |
| R2203–R2214 | Resistor | Gate drivers networks for M2202 and M2205 |
| U2201 | Comparator | Conditioned switch for HV to Free Hand Driver |
| R2201, R2202 | Resistor Divider | Divides logic level to match HV upper limit sense voltage above which Free Hand high voltage will not switch on |

TABLE 4

The Hand-Grasp Function Driver 214 (FIG. 5E) and the Standing Function Driver 216 (FIG. 5F)

| Component | Description | Circuit Function |
|---|---|---|
| U2301 | Crystal Oscillator Module, 13.5600 MHz | Controls Power Drive Frequency |
| U2302 | Dual Flip Flop | Divide Oscillator by 2 for 6.78 MHz ISM frequency and bi-phase drive for Class B output stage |
| R2301, R2304 | Resistors | Rf isolated logic input networks |
| U2303 | AND Gate Buffers | Output Stage Gate Driver |
| R2306–R2308 | Resistors | Gate Drive Hi-Low Through current limiters |
| R2309, R2310 | Resostors | Gate Pull-Downs |
| M2301, M2302 | Power MOS FETs | Class B Power Amplifier |
| C2307–C3211 L2301–L2303 | Passive Filter | Harmonic and Radiated Emission Suppression |
| C2305, C2305 | Capacitors | Local RF Bypass |
| B2301–B2305 | Ferrite Beads | Radiated Emission Suppression |
| R2302 | Resistor | Connection to DC continuity coil check |
| C2312 | Capacitor | RF Filter |

TABLE 5

The Microcontroller Module 204 (FIG. 5G)

| Component | Description | Circuit Function |
|---|---|---|
| C1201–C1205 | Capacitors | Microcontroller supply bypasses |
| C1206 | Capacitors | Local bypass for POWER RESET chip, U1202 |
| U1201 | Microcontroller | Provides all system control and interface |
| D1201, R1202 | R-Diode Network | Programming Pulse Interface |
| D1202 | Diode | Prevents Input drive when MPU is powered down |
| Y1201, | Quartz crystal, | MPU Clock reference and |

TABLE 5-continued

The Microcontroller Module 204 (FIG. 5G)

| Component | Description | Circuit Function |
|---|---|---|
| R1201 | 4.0 MHz and resistor | associated bias resistor |
| R1203, C1208 thru R1210, C1215 | R-C Networks | A/D Converter input Filter networks |
| C1216–C1222 | Capacitors | Spike filters on operator switch inputs |
| U1202 | IC, Power Monitor Reset | Monitors VDD and reset on power drops below 4.4 volts for 20 msec |
| U1203 | IC, 2.50 volt ref | Provides 2.5 volt A/D reference |
| C1207 | Capacitor | Noise Filter for A/D ref |
| R1211–R1213 | Resistors | Serial Buss Pull-Downs |
| R1222, R1223 | R-C Network | Pull-Up for Implant Coil Continuity check input |
| R1224, R1225 | Resistors | Daughter Bd. TP1, 2 Pull-downs |
| U1204 | IC, Serial EEPROM | Alterable non-volatile memory for setup preferences |
| R1214 | Resistor | Chip Select Pull-up (inactive) |
| U1205 | IC, IR and RS-232 interface | Provides serial IR send receive functions |
| D1203 | LED, IR | IR link IR emitter |
| R1216 | Resistor | Sets IR LED operating current |
| C1225 | Capacitor | Local bypass for IR transmit switching noise |
| C1224 | Capacitor | Local bypass for IR/RS-232 power |
| D1203 | Diode, IR photo | IR link IR detector |
| R1215, –17–18 | Resistors | Pull-Downs for U2105 control and data lines |
| U1208 | IC, remote control encrypte/decode chip | Decodes encrypted button application data |
| C1226 | Capacitor | Local bypass for remote control chip power |
| R1220, R1221 | Resistors | Pull-downs for U1208 control and data lines |
| U1206, U1207 | IC, 2-way switch | MPX Telemeter and IR communications to one set of MPU lines |
| R1219 | Resistor | Pull-downs for TEL-IR control line |
| J1201 | 2 × 15 Pos. Female | Option Daughter Board Jack |

TABLE 6

The User Interface Module (FIG. 5H)

| Component | Description | Circuit Function |
|---|---|---|
| U1301 | IC, 3.0 V regulator | Switches buzzer power |
| C1301 | Capacitor | Local bypass for buzzer regulator |
| C1302 | Capacitor | Filters switching noise within buzzer regulator |
| C1303, C1309 | Capacitors | Regulator Output Filters |
| R1301, R1308 | Resistors | MPU interface and Pull-Down |
| D1301 | Diode | Inductive spike clamp |
| LS1301 | Sound Transducer | Provides Audible Signal |
| U1302 | LCD Module | Provides Visual User interface |

TABLE 6-continued

The User Interface Module (FIG. 5H)

| Component | Description | Circuit Function |
|---|---|---|
| C1304 | Capacitor | Local bypass for LCD Module |
| R1302 | Resistor | LCD (Chip Sel) Pull-Up (inactive) |
| R1303, R1304 | Resistors | LCD and interface bias |
| U1303 | IC, 3.0 V regulator | Switches buzzer power |
| C1305 | Capacitor | Local bypass for buzzer regulator |
| C1306 | Capacitor | Filters switching noise within buzzer regulator |
| C1307, C1308 | Capacitors | Regulator Output Filters |
| R1306, R1307 | Resistors | MPU interface and Pull-Down |
| SW1301–SW1312 | SPST, MOM Push | User interface Buttons |
| SW1309–SW1312 | SPST, MOM Mag Reed | Alternate Control Mode |
| U1202 | IC, Power Monitor Reset | Monitors VDD and reset on power drops below 4.4 volts for 20 msec |
| J1301 | ZIF Jack, Ribbon | LCD Jack |

TABLE 7

The Infrared Transceiver 220 (FIG. 5K)

| Component | Description | Circuit Function |
|---|---|---|
| C1401 | Capacitor | Filter noise fed back to VDD |
| R1401 | Resistor | Pull-Down (disable) TEL, SHD (active <OFF> low) |
| U1401 | Linear Low Drop Regulator | Provides +3.0 volts for Transceiver Module, U1402 |
| C1402 | Capacitor | Filters switching noise within U1401 |
| C1403, C1409 | Capacitors | Regular Output Filters |
| R1403 | Resistor | Transmit, TELTXD Hi-Z pull-down |
| R1404 | Resistor | Transmit power set |
| R1402, C1404 | R-C Network | AGC Bias Supply and bypass |
| C1405 | Capacitor | Peak Detector Attack-Decay time constant |
| R1403 | Resistor | VBBO load isolation resistor |
| R1405 | Resistor | Sets Bandwidth of Baud Rate Low Pass Filter |
| R1406, R1108 | Resistors | Pull-ups for CT0 and CT1 Mode |
| R1401 | Resistor | RX DDATA Pull-Down |
| U1403 | Single 74 HCT equivalent OR Gate | Level translates RX DATA to 5 volt logic |
| C1406, C1407 | Capacitors | Antenna Tuning |
| ANT1401, –02 | Metal strips | Telemeter antenna elements |
| C1408 | Capacitor | Antenna match |

TABLE 8

Figures 1, 5M:
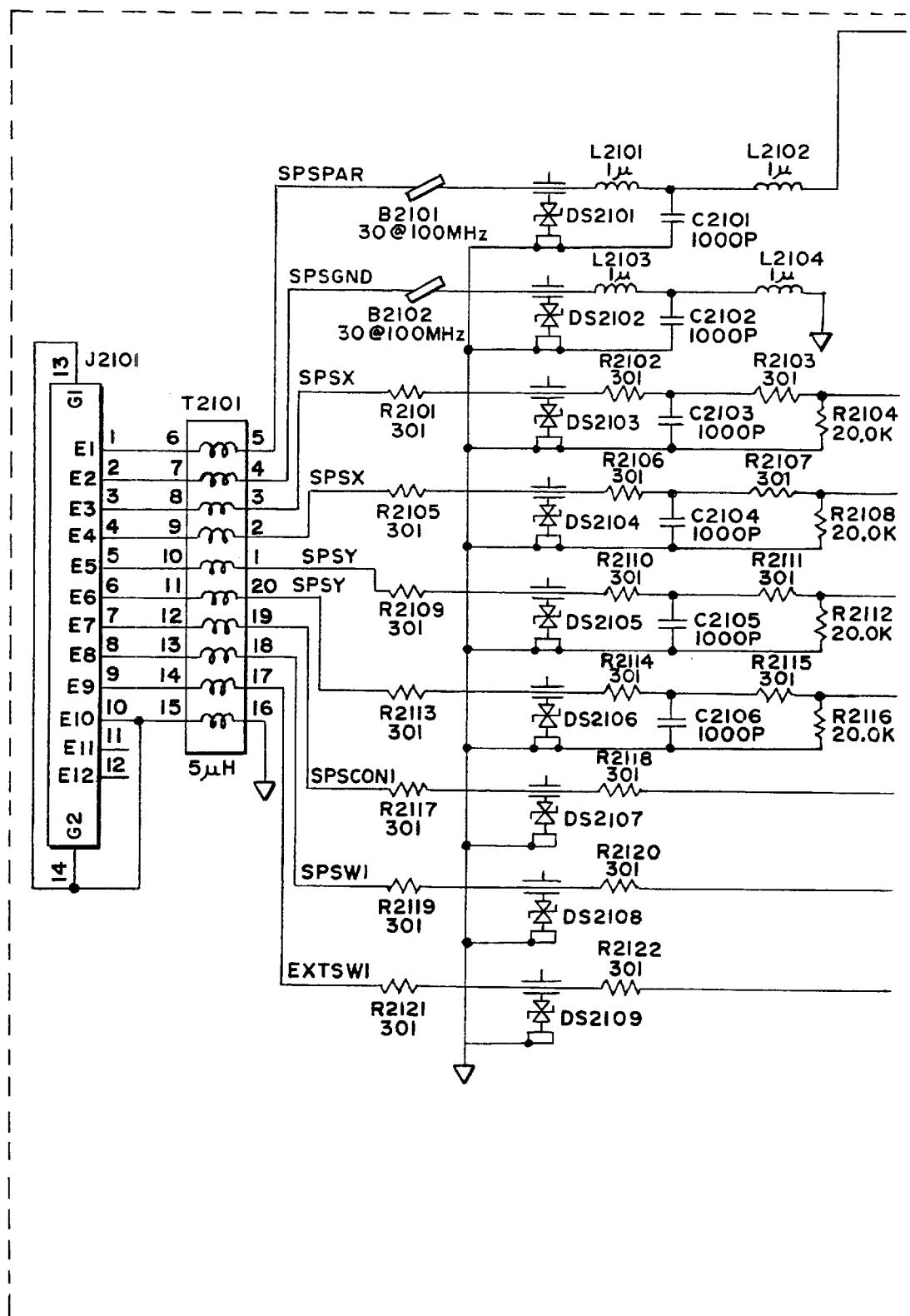
Figures 2, 5M:
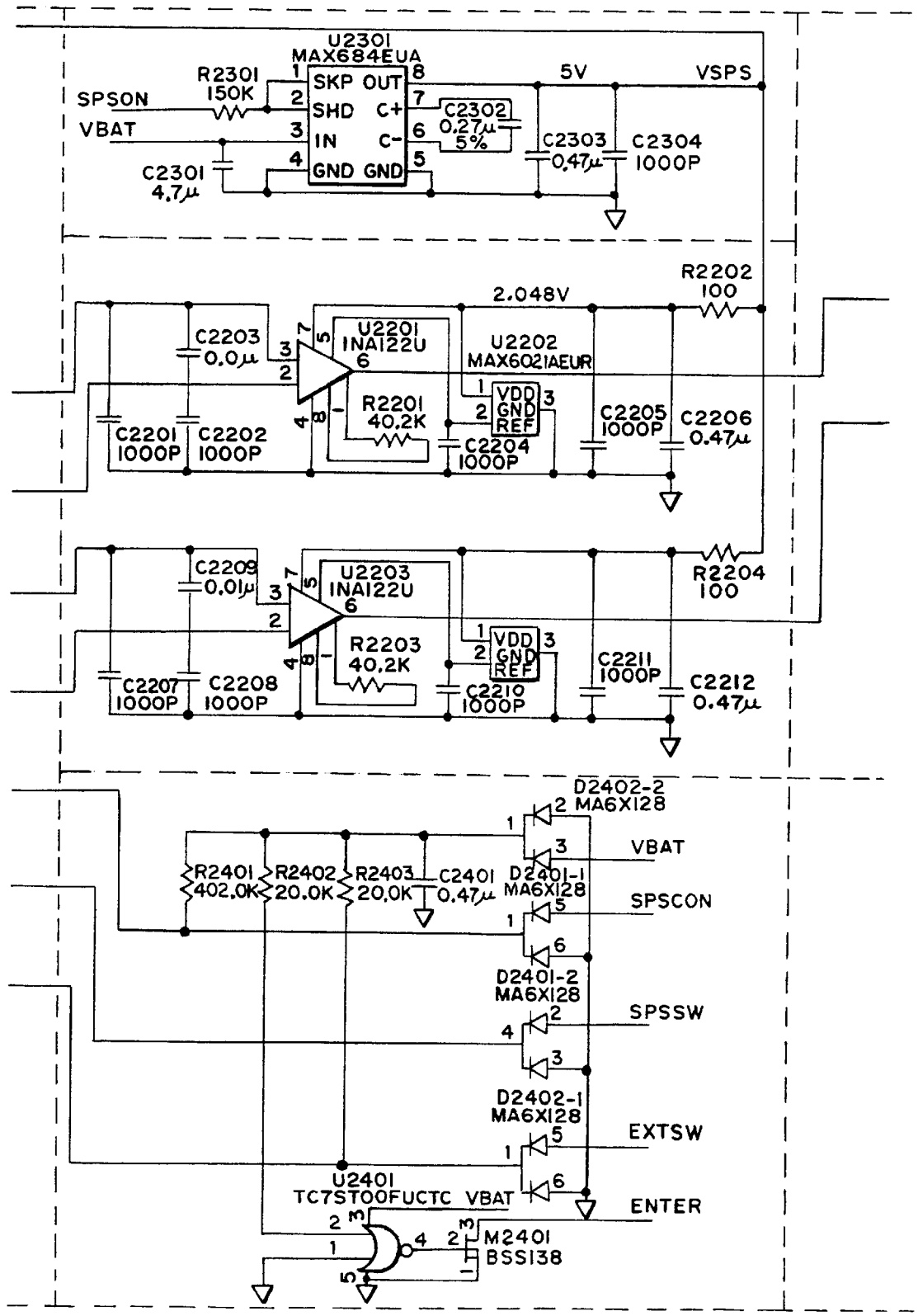
Figures 3, 5M:
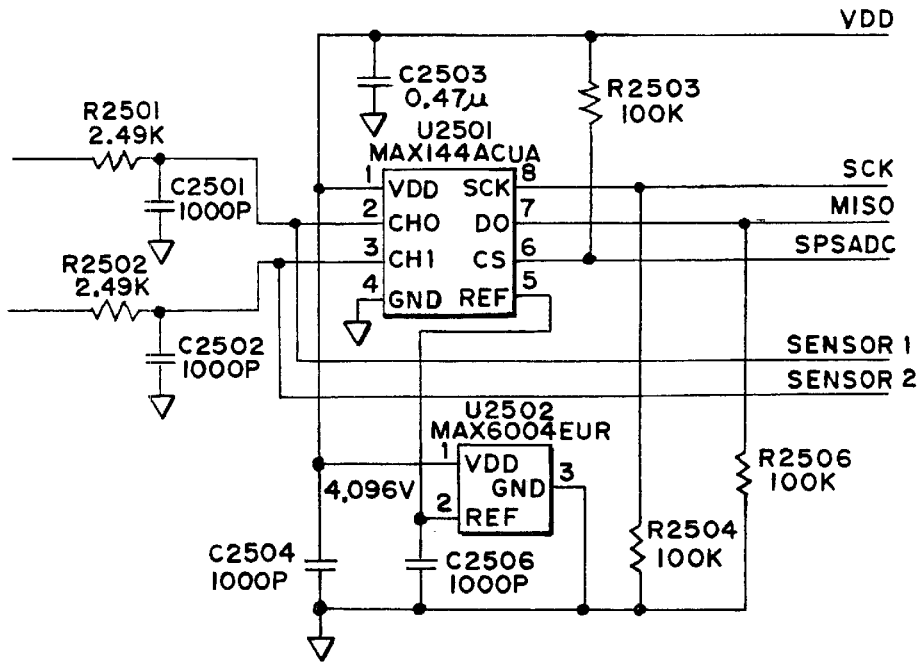

The Input Filter 230 (FIG. 5M)

| Component | Description | Circuit Function |
|---|---|---|
| J4101 | Jack, 14 pos, Female | Shoulder Position Transducer Module Input |
| B1401 | Ferrite Bead, 10 Lines | 1 × 10 Common Mode Choke, EMI suppression |
| DS4101–DS4109 | ZENER, TRANSIENT CLAMP 9 V | Protects Shoulder Position Diff. Amp. from transient discharge |
| L4101, L4103, C4101, C4110 and L4102, L4104 C4102, C4111 | L-C Networks | Filter DC Power and Ground lines to external Shoulder position Transducer Module |
| R4109, R4116 C4103, C4112 thru R4115, R4122 C4109, C4118 | R-C Networks | Filter Differential X and Y Signal and three switch closure signal lines from external Shoulder position Transducer Module |
| R4108, R4123 | Zero Ω Jumpers | EM Immunity Test Jumpers |

TABLE 9

The Differential Amplifier 232 and A–D Converter 234 (FIG. 5M)

| Component | Description | Circuit Function |
|---|---|---|
| U4102, U4104 | IC, Instrumentation Differential Amp | Shoulder Position Transducer Amplifier |
| F4205, –6 R4208, –9 | Resistors | Input pull down load, Amplifier |
| C4209, C4210 | Capacitors | Differential low pass filter |
| R4207, R4210 | Resistors | Gain Set, Differential Amplifier |
| U4203, U4205 | IC, Reference, 2.5 V | Pseudo Ground for U4102, U4104 |
| C4204, C4205 | Capacitors | Pseudo Ground noise Filter |
| U4201 | IC, Step up Charge Pump w/Linear Regulator | Provide switchable low noise power to Shoulder Position Transducer and Amplifier |
| R4204 | Resistor | SHD input over drive protection |
| C4201 | Capacitor | Local Bypass of noise fed back to battery voltage |
| C4202 | Capacitor | Charge Pump |
| C4203 | Capacitor | Regulator Output Bypass |
| U4206 | A/D Converter, 12 Bit/2 Ch Serial | Provides expanded resolution of Shoulder Position Amplifier Output |
| U4207 | IC, Ref., 4.096 V | Full scale ref., for U4106 A/D |
| C4206 | Capacitor | Full scale ref., noise Filter |
| C4207 | Capacitor | Local bypass for A/D Conv. |
| R4211–R4213 | Resistors | Serial Buss Pull UP and Downs |
| R4214 | Resistor | Board Identification Load |
| J4201 | 2 × 15 PIN, Male Bd. Mt Plug | Daughter to Main Bd. Connector |
| R4201–R4203 | Resistors | Pull-downs Switch closure lines |
| D4201–D4203 | Diodes, Signal | Reverse Drive protection for MPU |

2. The Firmware

The pre-programmed rules for the controller 26 (comprising the firmware) are contained in the EEPROM memory chip. The rules govern, e.g., the operation of the user interface, the generation of the stimulation timing and command signals by the supported function-specific utilities, the interface with the various function-specific control signal devices (including wireless links), the special modulation of pulse outputs, and communication with external programming sources. The control algorithms expressing the rules can be realized as a "C" language program implemented using the MS WINDOWS™ application.

The firmware, once embedded, can be reprogrammed or updated in various ways, including linkage (by cable or wireless infrared) of the controller 26 to an external computer with the appropriate software, or by the user using the keypad 34 on the controller 26 itself.

Further details of these representative implementations of these functional blocks of the controller firmware will now be described.

3. The User Interface

In the illustrated implementation (see FIG. 3A), the front shell 44 of the controller 26 presents the display 32 on which the various screens generated by the user interface are displayed. The user interface also displays on the screen 32 various graphic icons, e.g., a battery life icon 54, a stimulation energy application icon 76, and others (not shown), such an alarm or warning icon and a external computer connection icon. Associated audible signals can also be used to provide information regarding the status of these indications, e.g., low or discharged battery, errors, etc.

The front shell 44 of the controller 26 also presents the keypad 34, through which the user communicates with the interface. In the illustrated implementation (see FIG. 3A), six push buttons 56 to 66 are present. The push button 56 is used to turn the controller on. The button 56 also serves an enter key to progress from screen to screen of the interface. The push button 58 is used as to exit out of certain programming screens, as well as a control signal source in certain functions. The push buttons 60 and 62 are used to scroll up and scroll down the screens, to move through the menus generated by the user interface. The push bottons 64 and 66 are used to increment or decrement selections during certain functions. An audible signal or beep can be selectively generated upon pushing the buttons 56 to 66.

E. Task Selection Menu

Upon power up, the firmware displays an appropriate welcome screen (not shown) and executes a main loop, which continues to runs in the background at prescribed time intervals (e.g., every 16 msec). The main loop self-tests the microprocessor 36 for defective hardware or corruption of the flash memory contents. Errors noted by the main loop interrupt operation of the controller 26 and cause the user interface to display appropriate error icon and audible signal.

Absent an error during start up, the user interface function displays a Task Selection Menu 68 (see FIG. 3A) on the display screen 32. The Task Selection Menu 68 lists the specific therapeutic or prosthetic functions supported by the controller 26. In the illustrated implementation, the listed functions are (i) The Finger-Grasp Function; (ii) the Standing Function; and (iii) the Bladder and Bowel Control Function, as already described. The user selects a function by scrolling (operating the scroll buttons 60 and 62) and pushing the enter button 56. Upon selection, the firmware executes the function-specific processing utility dedicated to the selected function.

By way of example, the details of the processing utility dedicated the finger-grasp function will be described. Similar interface and control features can be executed to carry out the other functions.

In the illustrated implementation (see FIG. 6), the Opening Screen 70 for the finger-grasp function list four operational choices: Exercise; Function; Patterns; and Set Up.

1. Exercise

By selecting Exercise (using the scroll bottons 60 and 62 and the enter button 56), the screen displays an Exercise Regime Screen 72 (see FIG. 7), which also shows a time delay before an exercise regime is automatically initiated by the firmware. Different exercise regimes (designated Exercise 1, Exercise 2, Exercise 3, etc.) can be selected by the user by pressing the enter button 56 once within a predetermined short time interval (e.g., 3 seconds) after a given Exercise Regime Screen 72 is displayed. Typically, the timing parameters and exercise grasp patterns for each exercise regime have been preprogrammed into the firmware by a clinician, as will be described later.

With the desired exercise regime selected, the user presses the enter button 56 or waits for the time delay to expire. The display 32 shows an Exercise Underway Screen 74 to indicates that stimulation is being applied to carry out the selected exercise regime. The Exercise Underway Screen 74 displays a Stimulation On Icon 76, as well as the time remaining for the exercise session. As soon as the selected exercise regime is completed, the display 32 shows an Exercise Completed Screen 78.

After a prescribed time period of no further input (e.g., two minutes), the firmware turns the controller 26 off to conserve battery life. This automatic time-out feature is executed throughout the interface.

2. Patterns

Figure 8:
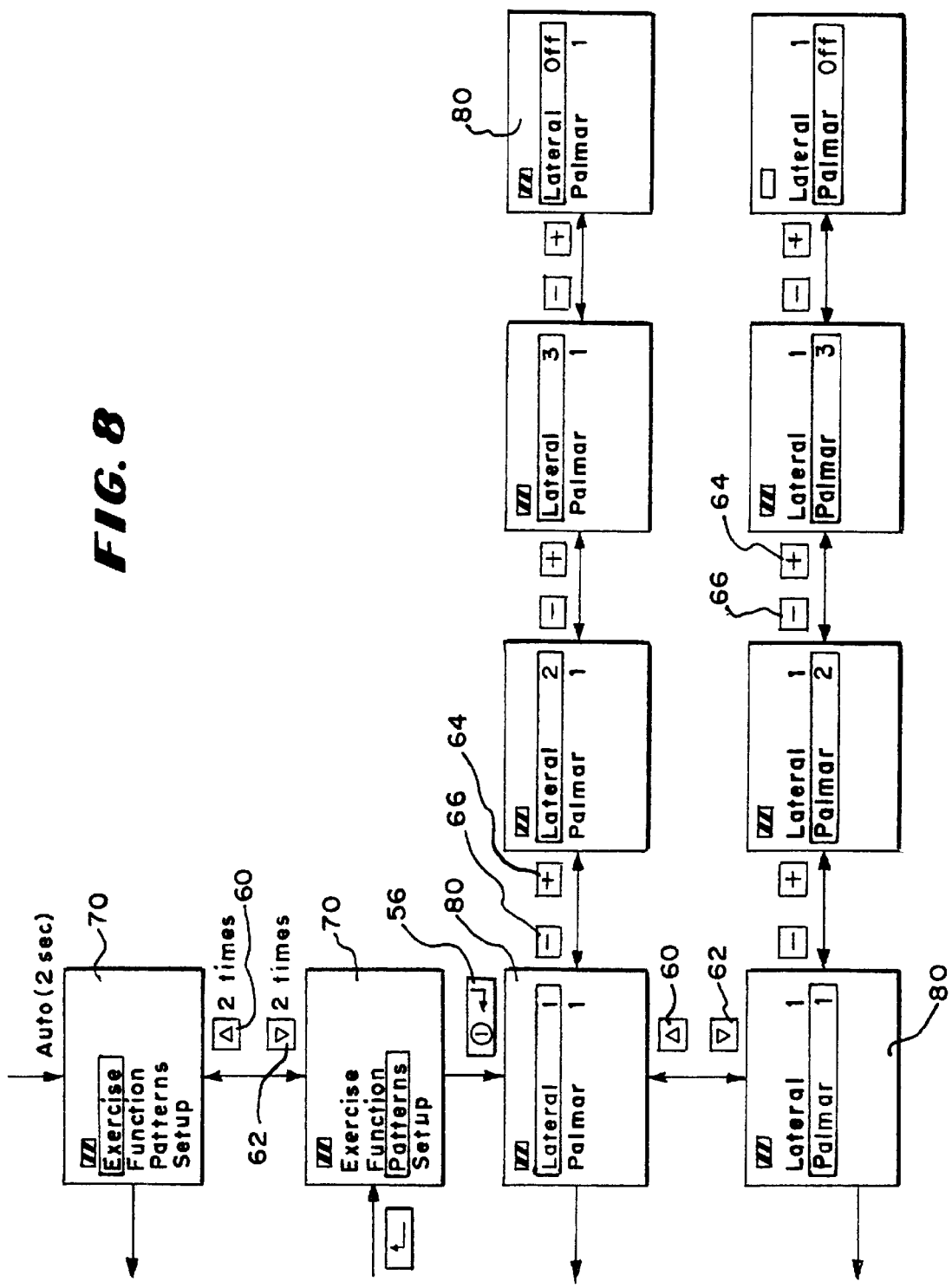
FIG. 8 is a view of the hierarchy of the Finger-Grasp Pattern screens of the user interface that the microprocessor shown in FIG. 5 generates, prompting the user to select from a list of different finger grasp functions that the universal external controller enables.

When Patterns is selected on the Opening Screen 70 (by use of the scroll buttons 60 and 62 and enter button 56) (see FIG. 8), the display 32 shows a Grasp Pattern Selection Menu 80 by which lateral and palmar grasp patterns can be selected. The Menu 80 lists "lateral" and "palmar" followed by numbers. The user scrolls using the buttons 60 and 62 to select either pattern. The user then increments or decrements using the buttons 64 and 66 to select the specific pattern by number. For example, there can be several lateral patterns (designated Lateral 1, Lateral 2, Lateral 3, and Lateral Off) and several palmar patterns (designated Palmar 1, Palmar 2, Palmar 3, and Palmar Off), which typically have been pre-programmed into the firmware by a clinician, as will be described later. When done choosing, the user selects the enter button 56, which returns to the Opening Screen 70 for the finger-grasp function.

3. Function

When a shoulder position sensor is coupled to the universal external controller 26 (designated as SW1 in FIG. 9), selection of Function on the Opening Screen 70 allows the user to control the finger-grasp function using the external shoulder position sensor. Typically, the clinician will have previously preprogrammed the controller 26 so that either back and forth shoulder movements or up and down shoulder movements sensed by the shoulder position sensor will generate the appropriate proportional commands to open and close the grasp. The clinician may also have preprogrammed the controller so that quick movements of the shoulder position sensor will lock the grasp. Alternatively, the clinician may have preprogrammed the controller to lock the grasp in response to input from a remote lock switch (designated as SW2 in FIG. 9) coupled to universal external controller 26. The remote lock switch toggles the existing grasp pattern between a locked and unlocked position, and can be used by individuals who have difficulty with or do not want to use the shoulder jerk motion.

With the Function selected, the user turns the shoulder position sensor on. The firmware responds to shoulder movement input in either elevation/depression or protraction/retraction to grade hand position and strength from opened to closed. Thus, for example, by retracting the shoulder, the hand opens, and by protracting the shoulder, the hand closes.

Figure 9:
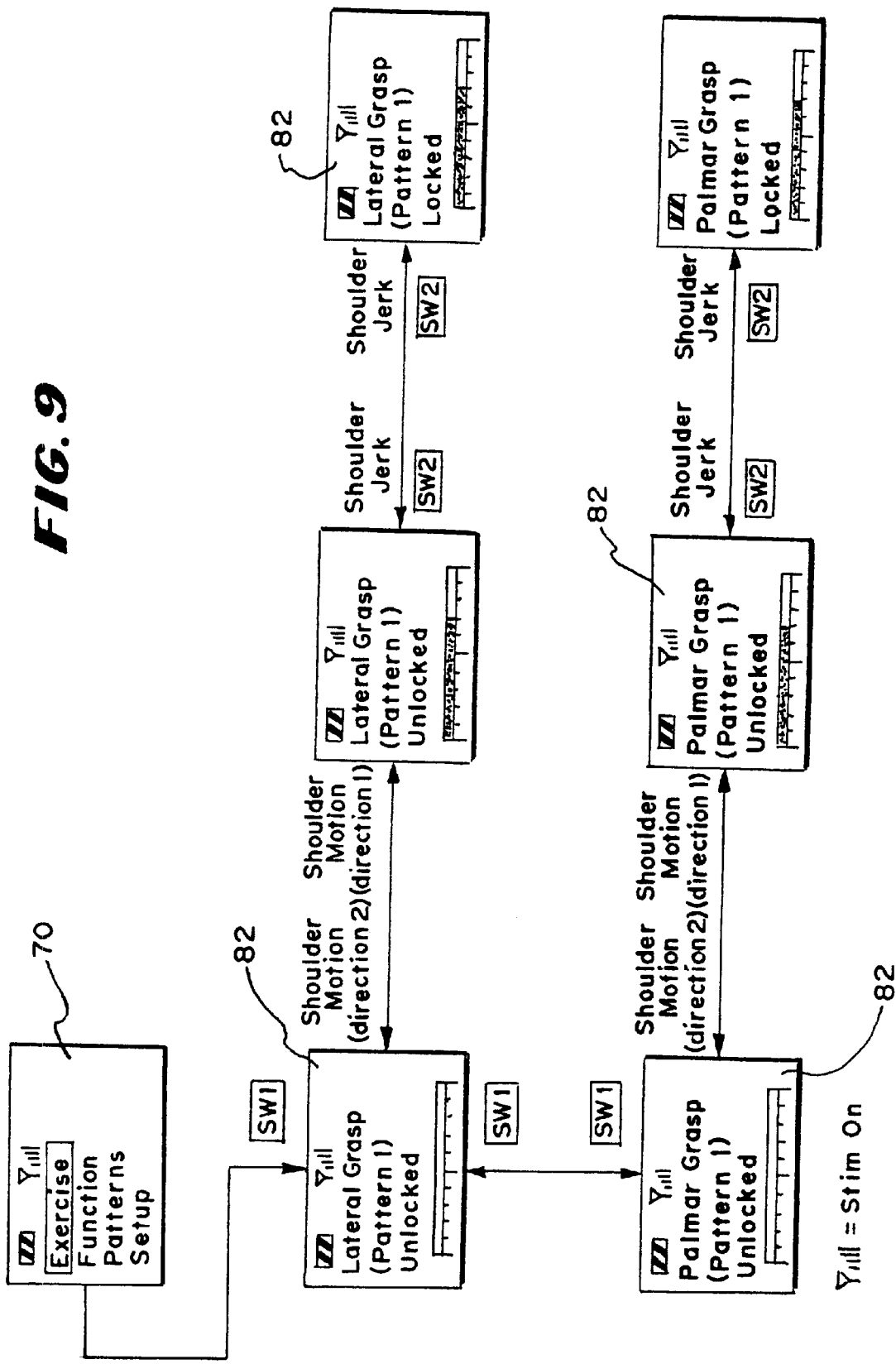
FIG. 9 is a view of the hierarchy of the screens of the user interface that the microprocessor shown in FIG. 5 generates, as the user affects different finger-grasp control functions using a shoulder position sensor as the control signal source.

In response to shoulder movement, the firmware turns the stimulation on to undertake the last selected lateral grasp pattern. The firmware executes a proportional control algorithm that, in response to the prescribed shoulder movement (e.g., protracting the shoulder), applies stimulation to progressively close the user's hand in the desired grasp pattern. Changing the prescribed shoulder movement (e.g., retracting the shoulder) changes the execution of the proportional control algorithm to apply stimulation to progressively open the hand. The hand can be thereby progressively opened or closed in this manner. Pressing a switch on the shoulder sensor will toggle between lateral and palmar grasp patterns As shown in FIG. 9, a Grasp-Function Status Screen 82 is displayed as the control algorithm is being executed. A graphical depiction on the Grasp-Function Status Screen 82 (which, in the illustrated embodiment, comprises a directional arrow and a bar chart) proportionally tracks the grasp position of the hand from open to closed, and vice versa. The Grasp-Function Status Screen 82 also displays the current grasp pattern. The Stimulation On icon 76 is also displayed.

If so programmed, a small quick shoulder motion will lock the grasp in the then-existing position, and the Grasp-Function Status Screen will accordingly change to indicate the grasp is "locked." With the grasp locked, the user is able to move the shoulder without altering the then-existing grasp pattern. When the user wants to regain control of the hand, a subsequently small quick shoulder motion will unlock the grasp, and the grasp function resumes according to the prescribed shoulder movement from the then-existing position. The Grasp-Function Status Screen 82 changes to indicate that the grasp is "unlocked" and the proportional direction display resumes. Alternatively, if so programmed, depressing a remote lock switch will cause the grasp to lock and unlock.

Desirably, according to preprogrammed rules in the firmware, when the unlock command has been given, the grasp command enters a realignment state, during which the existing position of the grasp will not change until the user moves the shoulder back to the position where the lock command occurred. This keeps the user's hand from step-jumping opened or closed until the user is prepared to control it. Alternatively, the realignment state can be automatically implemented, during which, upon receiving an unlock command, the firmware aligns the grasp command range with the user's current shoulder position. The position of the command range can be automatically adjusted during proportional control, too. These options are selectable during programing of the firmware.

Appropriate audio signals can be also generated by the controller to mark changes in the stimulated grasp pattern from open to close, locked and unlocked, lateral and palmar.

Holding the enter button 56 for a predetermined time (e.g. 2 seconds) turns the controller 26 and the ongoing stimulation off. Holding the switch on the shoulder position sensor for a prescribed period will also turn the ongoing stimulation off.

If a shoulder position sensor is not coupled to the universal external controller 26, the user can subsequently control a selected grasp pattern by using the keypad 34 on the controller 26 itself.

Figure 10:
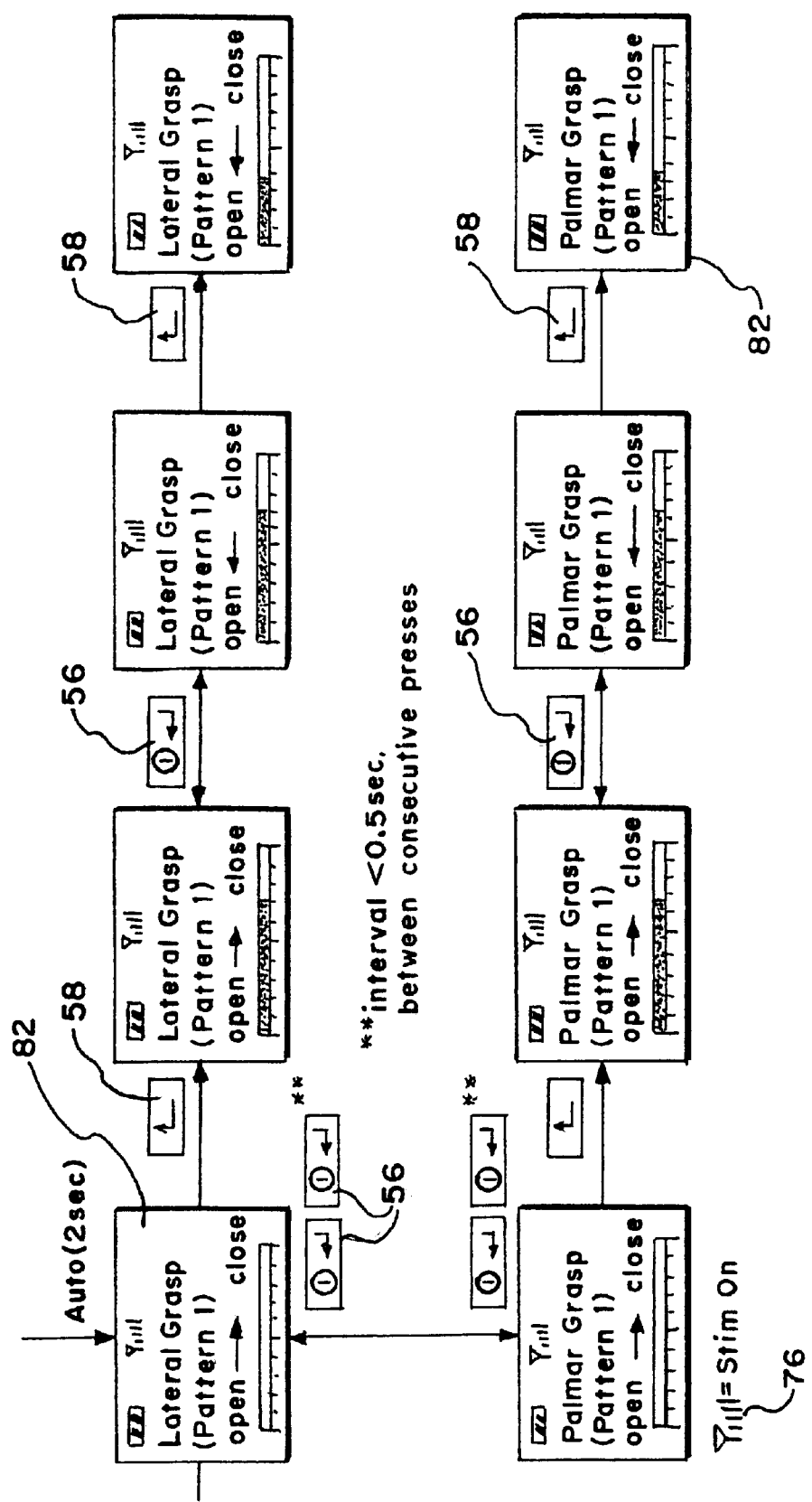
FIG. 10 is a view of the hierarchy of the screens of the user interface that the microprocessor shown in FIG. 5 generates, as the user affects different finger-grasp control functions using the keypad of the universal external controller as the control signal source.

In a representative implementation, with the Opening Screen 70 for the finger-grasp function displayed, depressing the enter button 56 for a prescribed time period (e.g., 2 seconds) turns the stimulation on to undertake the last selected lateral grasp pattern. As FIG. 10 shows, the Grasp-Function Status Screen 82 is displayed, as previously described. The firmware executes a gated ramp control algorithm that, in response to pressing or holding the control button 58, applies stimulation to progressively close the user's hand in the desired grasp pattern. Pressing the enter button 56 changes the execution of the gated ramp algorithm to apply stimulation to progressively open the hand. The hand can be progressively opened or closed in this manner. The graphical depiction on the Grasp-Function Display Screen 82 (i.e., in the illustrated embodiment, the directional arrow and a bar chart) proportionally tracks the grasp position of the hand from open to closed, and vice versa. Pressing the enter button 56 twice while executing a grasp function toggles between a selected lateral or palmar grasp pattern. The Grasp-Function Display Screen likewise displays the current grasp pattern and the Stimulation On Icon 76.

By releasing the enter button 56 as the hand is opening or closing, the gated ramp algorithm locks the hand at the then-existing grasp position, and the Grasp-Function Status Screen 82 accordingly indicates that the grasp is "locked." When the user wants to regain control of the hand, a subsequently pressing the enter button 56 resumes the grasp function in the last selected direction from the last-existing position. Upon receiving a lock command, the gated ramp control algorithm maintains the grasp as the last-existing command level until it receives a further command from the keypad 34 to unlock the grasp pattern or to turn the controller 26 off.

Holding the enter button 56 for a predetermined time (e.g. 2 seconds) turns the controller 26 and the stimulation off.

4. Setup

The firmware can permit an individual user to program designated functions of the controller using the keypad 34. The extent to which the firmware allows this will vary according to degree of freedom the manufacturer or clinician wants to provide an individual user.

Selection of Setup in Opening Screen 70 (using the scroll buttons 60 and 62 and control button 58) permits this function. In one representative implementation, the firmware allows the user to customize the controller 26 by (i) selecting the grasp lock control input source; (ii) disabling sound that accompanies use of the keypad 34 or shoulder position sensor; (iii) or changing the volume of audible feedback.

Figure 11:
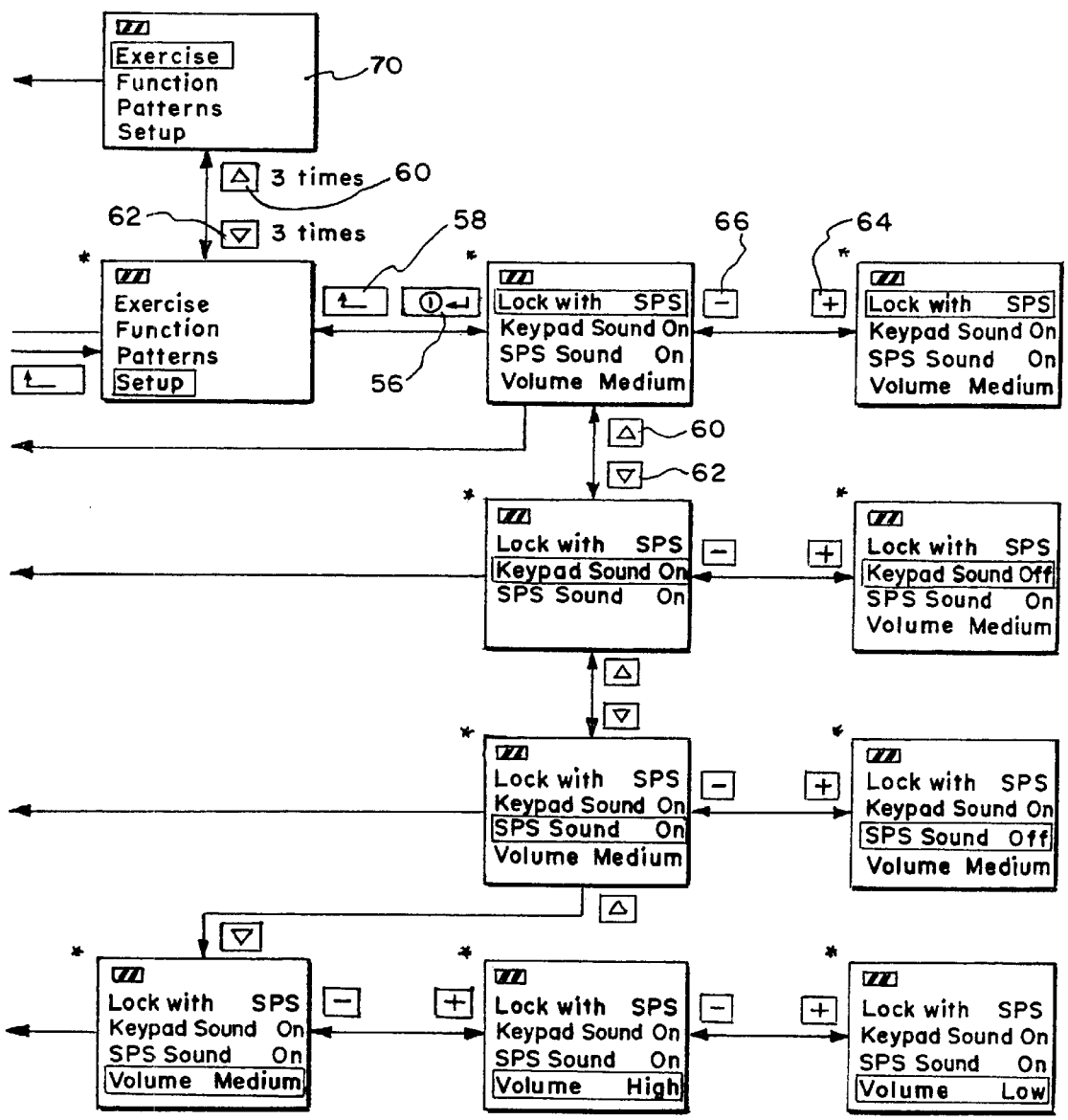
FIG. 11 is a view of the hierarchy of Set Up screens of the user interface that the microprocessor shown in FIG. 5 generates, which allow the user to select and change certain operating states or conditions of the user interface of the universal external controller.

Selection of Setup displays a Selection Menu Screen 84 (see FIG. 11), where the permitted reprogramming selections are listed. By scrolling to the appropriate selection (using buttons 60 and 62), incrementing or decrementing the associated status selections (using buttons 64 and 66), and by selecting (by pressing the enter button 56), the various reprogramming selections can be accomplished. For example, the user can choose to lock the grasp using an external switch or by shoulder motion itself; or turn the keypad sound on or off; or turn the audible feedback for shoulder sensor movement on or off; or adjust audible feedback volume from medium or high.

F. Interface with the Control Signal Devices

The universal external controller 26 can accommodate input from a variety of external control sources, such as myoelectric surface electrodes, remote control switching devices, reed switches, and push buttons on the user interface panel of the universal external controller 26 itself. External control sources can be coupled to the universal external controller 26 by direct (i.e., cable) connection, or by wireless link (e.g., 900 MHz).

G. Communication with External Programming Sources

Figure 12:
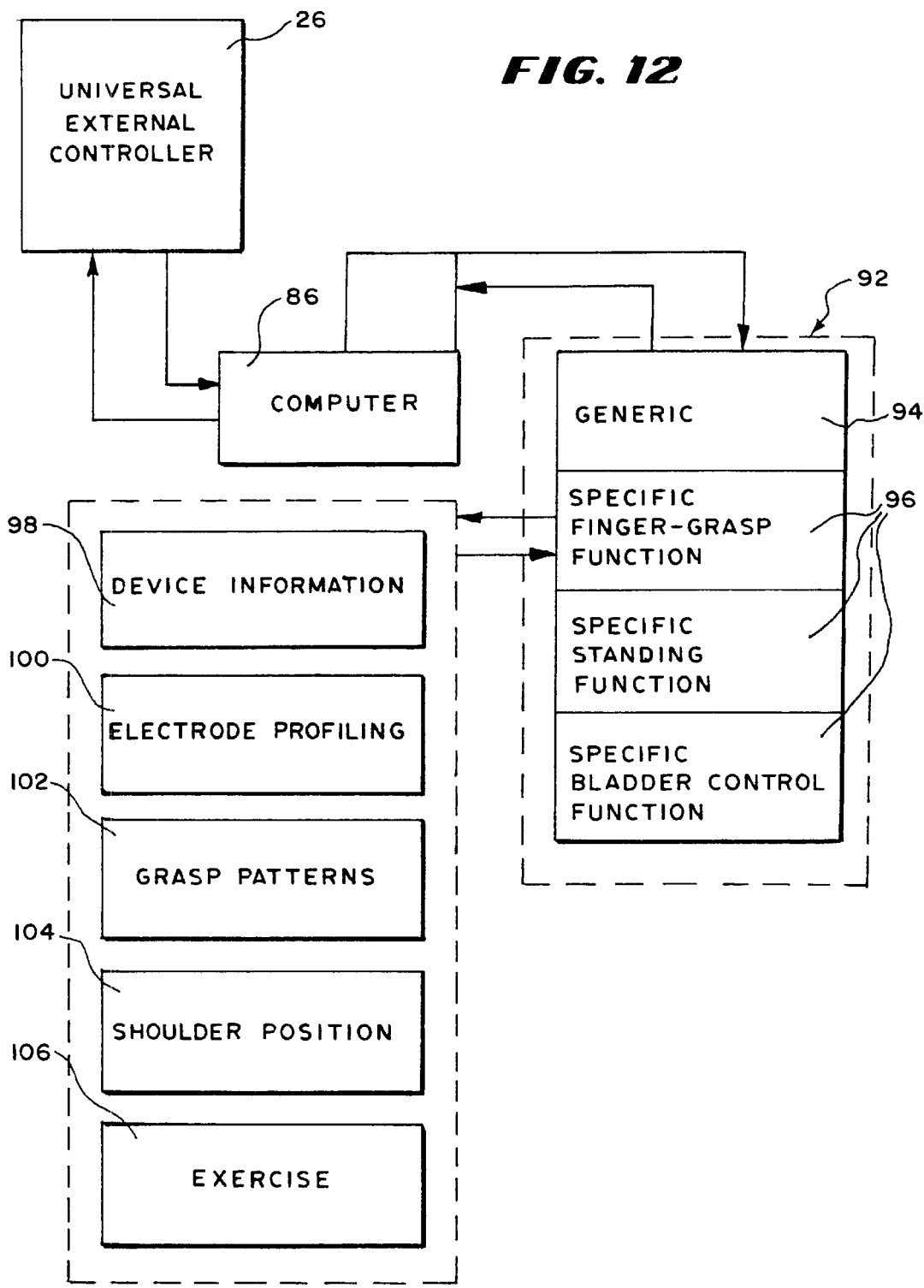
FIG. 12 is a schematic view of a remote programming system, which can be used in association with the universal external controller shown in FIGS. 3A to 3C, to control, monitor and program the universal external controller.

When the universal external controller 26 is not otherwise engaged in the execution of a functional task, the controller 26 can be linked to a remote computer 86 for programming by a clinician (see FIG. 12).

The link can comprise a hardware interface, e.g., an interface module and serial cable to route and translate data between the remote computer 26 and universal external controller 26. Alternatively, the firmware of the universal external controller 26 allows communication through an infrared link, thereby eliminating the need for an interface module, serial cable and any direct hardware connection. The infrared link simplifies communication and eliminates electrical safety concerns associated with direct electrical connection.

Figure 13:
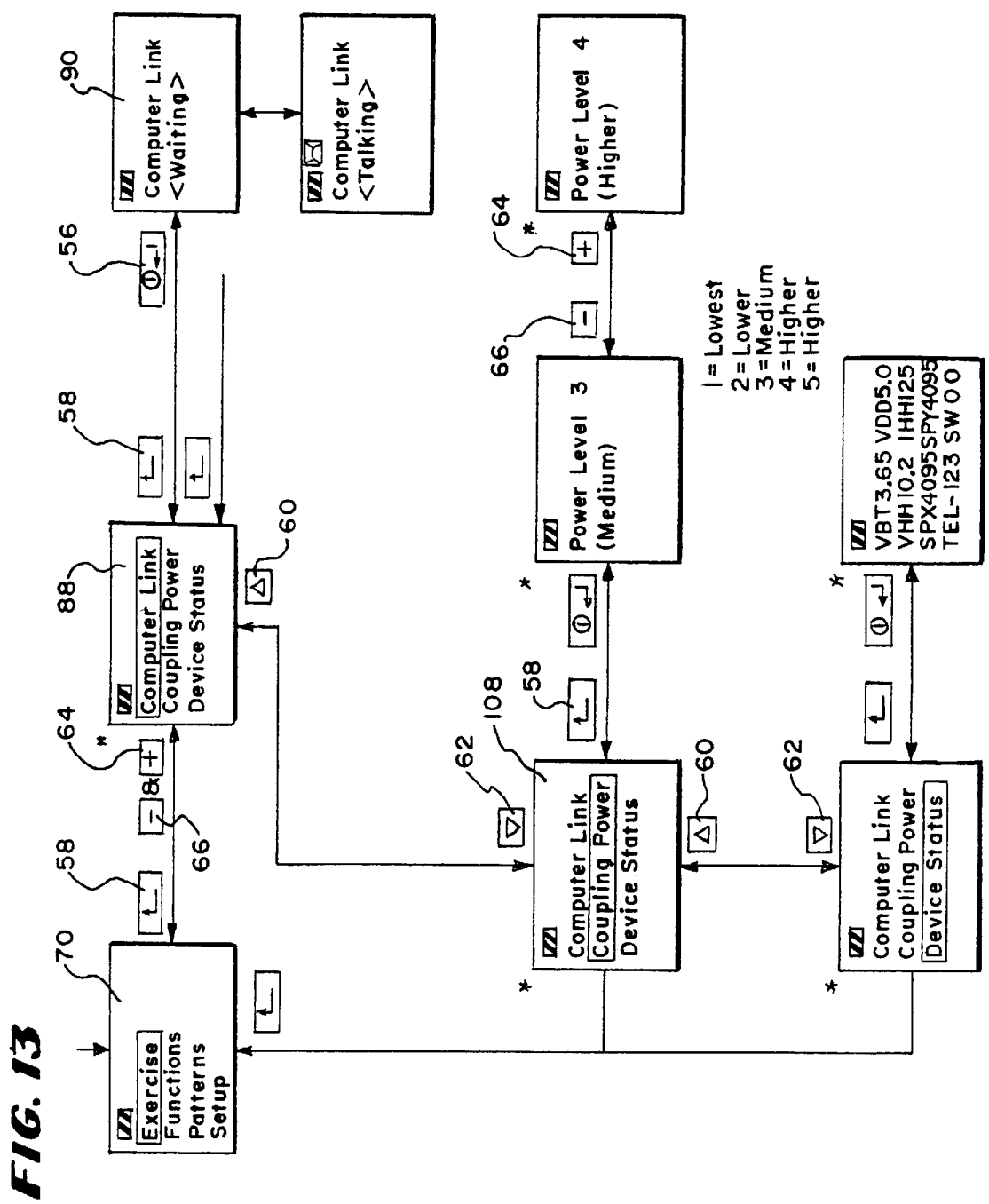
FIG. 13 is a view of the hierarchy of the screens of the user interface that the microprocessor shown in FIG. 5 generates, which allow the user or a trained technician to input programming instructions to the microprocessor, so that operation of the universal external controller can be customized and optimized.

The firmware establishes communication with the remote computer 86, to identify and qualify incoming information received from the remote computer 86. The interface desirably includes a Clinician Set Up Screen 88 (see FIG. 13), which is displayed upon pushing the control button 58 when in the Opening Menu 70 for a given selected function. The Clinician Set Up Screen 88 shows a Computer Link prompt, which can be selected by use of the buttons 64 and 66 and control button 58 to show a Computer Link Status Screen 90. The Computer Link Status Screen 90 indicates "waiting" and then "talking" as the link between the universal external controller 26 and the remote computer 86 is established.

In the illustrated implementation (see FIG. 12), the remote computer 86 desirably executes a programming system 92, which can be used to control, monitor and program the universal external controller 26 in the selected function. The programming system 92 allows a clinician to customize the firmware residing in an individual universal external controller 26 according the specific needs of the user and the treatment goals of the clinician. The primary purpose of the programming system 92 is to adjust parameters and store the parameters affecting the selected function in the universal external controller 26, which is used by the patient during daily operation. The system 92 also desirably provides an interface to display visual feedback to the clinician and user about the operation of the control algorithms and equipment associated with the controller 26.

In a representative implementation, when the finger-grasp function is selected, and the universal external controller 26 and remote computer 86 are linked, the programming system 92 can be run to assess the muscle recruitment patterns, set grasp stimulation patterns, adjust controller parameters, set exercise timing, and retrieve usage data resident in the firmware affecting the finger-grasp function. The programming system 92 enables inputs from the universal controller 26 to be monitored and stimulus outputs to be controlled in real time. The programming system 92 also allows operational parameters to be saved to an electronic patient file and downloaded to the universal external controller 26. The universal external controller 26 can then be disconnected from the programming system, allowing portable operation, as already described.

Desirably, the programming system 92 can be installed on a personal computer (e.g., a 233 MHZ Pentium II laptop with 800×600 resolution monitor) running Microsoft Windows™ 98 or higher. The programming system 92 desirably includes a clinician programming interface, which allows allows the clinician to observe, modify, and program the stimulus patterns, the shoulder position control characteristics, and the exercise sequences in an expeditious and user-friendly way. In a representative implementation, the clinician programming interface can be written in the Visual Basic 6 programming language for execution in the Windows environment.

In the illustrated implementation (see FIG. 12), the system is composed of a generic module 94 including generic patient information and as well as one or more specific modules 96 for each of the function-specific tasks supported by the controller 26 (e.g., the finger-grasp function, the standing function, and the bladder and bowel control function).

The generic patient information module 94 stores all general information about the patient using the particular universal external controller 26. The information in this module 94 does not necessarily relate to any particular function-specific device, but includes, e.g., fields for entering personal information that the patient may prefer to keep confidential.

The number and nature of the specific modules 96 will vary according to the number and nature of the function-specific tasks that the controller 26 supports. By way of example (see FIG. 12), for the finger-grasp function, there can be a system device information module 98, an electrode profiling module 100, a lateral and palmar grasp patterns programming module 102, a shoulder position sensor programming module 104, and an exercise programming module 106. Appropriate counterpart modules can also provided for the other treatment functions supported by the controller 26.

For the finger-grasp function, the device information module 98 captures, stores, displays, and allows modification of information that relates to the components arranged to accomplish the finger-grasp function system, including surgical implantation procedures, device serial numbers, electrode mapping, and progress notes. For the finger-grasp function, the remaining modules 100 to 106 allow optimization and programming of functional features of the components.

The electrode profiling module 100 aids the clinician in determining the stimulation thresholds and operational range of parameters for each electrode implanted on a muscle. This information determines system performance and configures electrodes for grasp programming. For example, for each electrode, the maximum force that can be obtained from the electrode during use can be determined, as can specific points of interest (POI) of the recruitment characteristics of each muscle. For each electrode/muscle, the threshold for recruitment and the maximum desired force is determined for each grasp pattern. Additional POI's can be denoted such as spillover to other muscles and other comments.

The grasp programming module 102 provides a mechanism for the clinician to program, view, and modify grasp patterns. The grasp pattern coordinates the activity of the muscles implanted with electrodes to produce different functional grasp, e.g. lateral and palmar grasps. The main functions of the module 102 are to program, view, and modify the activation level of each electrode as a function of percent command. This module 102 provides templates and example grasps that the therapist can modify for the individual patient. The therapist can then test the pattern, compare to previous patterns, and modify the pattern before transferring them to the universal external controller 26.

The shoulder position sensor programming module 104 provides a mechanism for the therapist to program, view, and modify the shoulder position proportional control and lock parameters. The module 104 allows the therapist to determine the patient's range of shoulder motion, select control and locking directions, select stationary or mobile command, display visual feedback to aid the patient in understanding the operation of the shoulder controller, set the parameters for locking the grasp, test the shoulder position sensor settings, both with and without an active grasp, and compare the new settings with previous settings.

The exercise programming module 106 enables the therapist to program, view, and modifying patient exercise routines. The main functions of this module 106 include setting exercise duration, setting the delay in starting the exercise, selecting the exercise patterns, and selecting specific exercise timing parameter. It also allows the therapist and user test the exercise patterns prior to programming.

In the illustrated implementation, the Clinician Set Up Screen 88 (see FIG. 13) also includes a Coupling Power prompt. When selected (using the buttons 60 and 62 and the control button 58), a Coupling Power Select Screen 108 is displayed. The Screen 108 allows the clinician (using the increment/decrement keys 64 and 66 and control button 58) to select an appropriate couple power setting, from 1 (lowest) to 5 (highest). The clinician can thereby adjust the power output of the pulse transmitter 16 for the selected function. The controller 26 is thereby able to adjust to different different depths of implantation for the receiver/stimulator for a given function, which, in turn, dictate different radio frequency power levels to transcutaneously link the receiver/stimulator for that function to the associated pulse transmitter for that function. The clinician is thereby able to customize the controller 26 to optimize reliable coupling while maximizing battery life.

In the illustrated implementation (see FIG. 13), the Clinician Set Up Screen 88 also includes a Device Status prompt. When selected (using the buttons 60 and 62 and control button 58), a Device Status Screen 110 is displayed. Information on the Device Status Screen 110 allows the clinician to assess the operating state of the controller 26 for monitoring and trouble shooting purposes.

H. Power Conservation

In addition to the allowing optimization of coupling power (as just described), the firmware also incorporates preprogrammed rules that promote other power conserving techniques aimed at prolonging battery life. In the illustrated embodiment, the power conserving techniques includes pulsed signal output (to the receiver/stimulator) and pulsed signal input (from the control signal source).

1. Pulsed Signal Output

As previously described, under the control of the preprogrammed rules in the firmware of the microprocessor 36, the universal external controller 26 governs the hand-grasp function by generating prescribed stimulus timing, command, and power signals based upon input received from the shoulder position sensing control signal source.

The prescribed stimulus timing, command, and power signals are formatted for transmission by the function-specific pulse transmitter in the form of modulated radio frequency carrier wave pulses. By pulsing the output command signal for the hand-grasp function, the universal controller conserves power, to thereby conserve battery life.

Figure 14A:
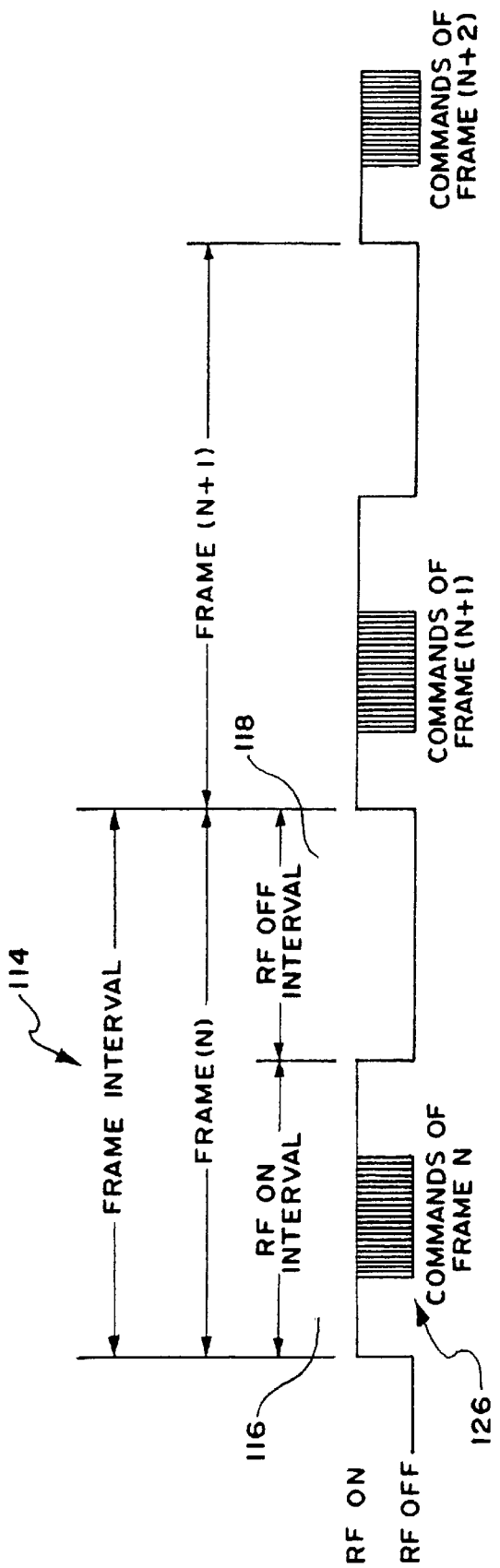

As shown in FIG. 14A, the output command signals are transmitted during successive frame intervals 114. Each successive frame interval includes 114 an ON period 116, during which radio frequency energy is generated to transmit the command signals to the function-specific pulse transmitter, and an OFF period 118, during which no radio frequency energy (and thus no command signals) are being transmitted. The duration of the frame interval 114 can vary. In a representative embodiment, the ON periods 116 and OFF periods 118 begin on 1 msec boundaries, so that the frame interval 114 is an integer multiple of 1 msec. The frame rate is set to equal the stimulus frequency, which equals 1/Frame Interval. In a representative embodiment, the stimulus frequency is 6.78 MHz±5 KHz.

Figure 14B:
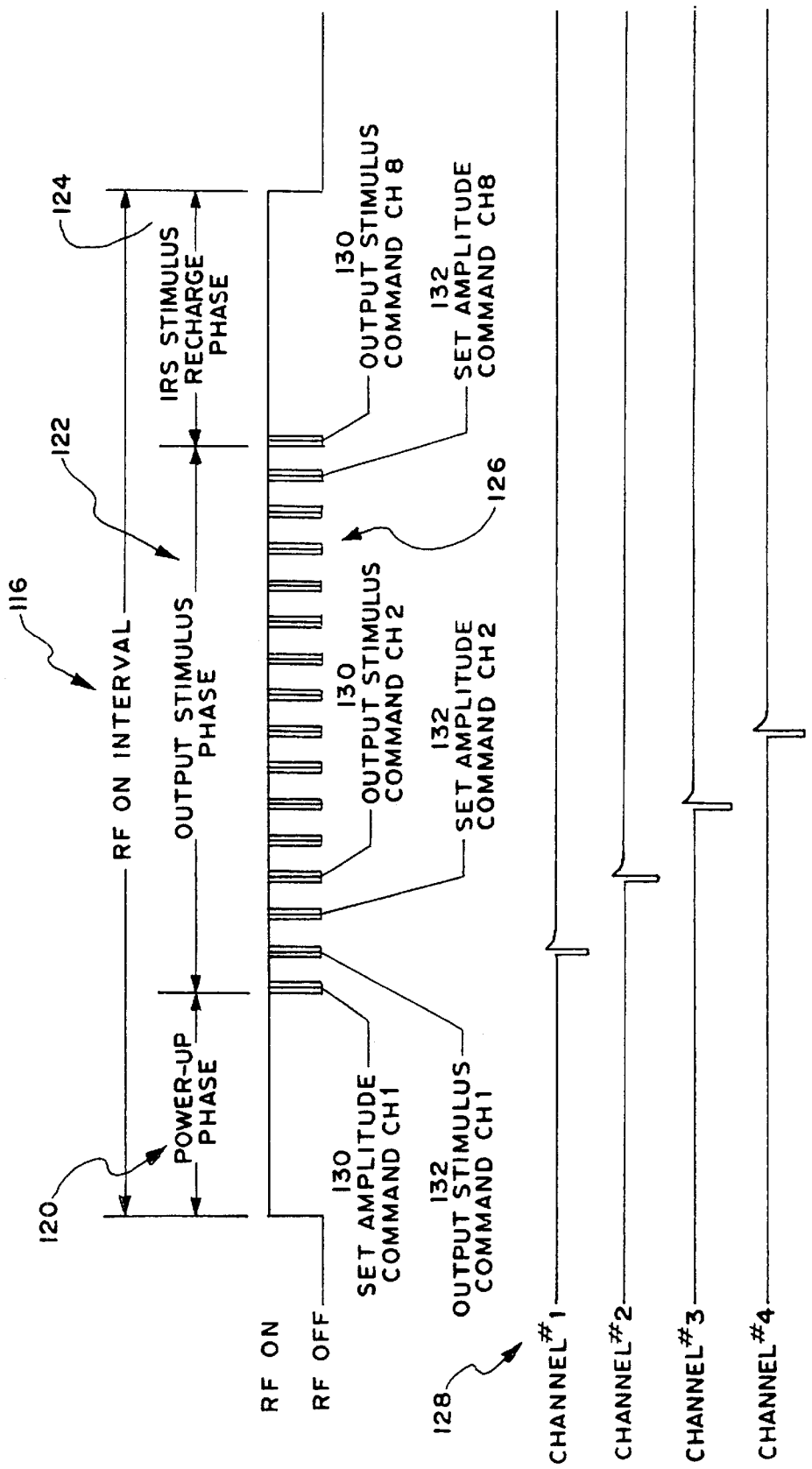

Within each ON period 116 of a given frame interval 114 (see FIG. 14B), there is a power up phase 120, followed by an output stimulus phase 122, followed by a recharge phase 124 (to allow for radio frequency magnetic field decay). The command signals 126 are transmitted only during the output stimulus phase 122. The command signals 126 are transmitted in channel groups 128, with a channel 128 group dedicated to a given implanted electrode where stimulation is to be applied. Each channel group 128 includes a set amplitude command 130 and an set duration command 132. The length of the output stimulus phase 122 will, of course, depend upon the number of channels receiving stimulation and the nature of the stimulation. When a channel has no command output (i.e., there are no set amplitude or duration commands for that channel), the next higher stimulation channel assumes its time slot.

In the illustrated embodiment, all commands begin on 1 msec boundaries (as previously stated). Representative time periods for the phases are, for the power up phase 120: 16 msec in duration if the OFF period 118 is more than 52 msec in duration, otherwise, 6 msec; for the output stimulus phase 122: 2 times N msec in duration, where N is the number of channels being stimulated; and for the recharge phase 124, 10 msec in duration. As frame rates increase, the OFF period 118 will become shorter until there is no OFF period 118.

Within each channel group 128, the set amplitude command 130 and the set duration command 132 are arranged within a pulse window 134 (see FIGS. 14C and 14D). The initial period of the pulse window includes a coding window 136. The preprogrammed rules of the firmware generate successive radio frequency pulses during which radio frequency energy is applied (RF ON) and during which radio frequency energy is not applied (RF OFF). In a representative embodiment, the total interval for a given RF ON and RF OFF sequence is 10 μsec (±1 μsec), and the RF ON interval within this period is 4 μsec (±1 μsec). Gaps 140 are formed between the RF ON and RF OFF periods, which in the representative embodiment last 6 μsec (±1 μsec). The pre-programmed rules of the firmware establish the set amplitude command and the set duration command depending upon the number and sequence of gaps 140 in the pulse window 134.

The coded correlation prescribed between the number and sequence of gaps 140 and the related commands can, of course, vary. In a representative implementation (see FIG. 14C), a succession of two to nine gaps 140 in the initial coding window 136 prescribe the channel for which a set duration command 132 is to be effective. Two to nine gaps 140 identify channels 1 to 8, respectively (i.e., two gaps means channel 1, three gaps means channel 2, and so on). In FIG. 14C, seven gaps identify a set duration command for channel 6.

As further shown in FIG. 14C, the succession of channel gaps 140 in the coding window 136 is followed by a gap 142 having a length (i.e., duration) which sets the actual duration of the stimulation pulse that is to be applied to the prescribed channel. The length of the gap 142 outside the coding window 136 can vary, e.g., between 1 μsec to 200 μsec. In FIG. 14C, the gap 142 outside the coding window 136 is shown to be 65 μsec, which specifies a stimulus duration of 65 μsec.

In the representative implementation (see FIG. 14D), a succession of eleven gaps 140 in a successive coding window 136 prescribes the amplitude of the pulse that is to be applied to the earlier prescribed channel. As FIG. 14D shows, following the eleven gaps 140 in the coding window 136 is another succession of gaps 144 outside the coding window 136, the number of which set the pulse amplitude. For example, in the representative implementation, eleven gaps 140 in the coding window 136 followed by one gap 144 sets an amplitude of 14 mA; eleven gaps 140 in the coding window 136 followed by two gaps 144 sets an amplitude of 8 mA; eleven gaps 140 in the coding window 136 followed by three gaps 144 sets an amplitude of 2 mA, and eleven gaps 140 in the coding window 136 followed by four gaps 144 sets an amplitude of 20 mA. In FIG. 14D, a pulse amplitude of 2 mA is set.

In a representative embodiment, each pulse window 134 is assigned a duration of at least 410 μsec. Within the pulse window 134, the initial coding window 136 is assigned a duration of 150 μsec (±5 μsec).

2. Pulsed Single Inputs

The input from the shoulder position sensor can also be pulsed, to conserve power consumption. In the illustrated embodiment, as already explained, the power supply 236 on the auxiliary board 40 converts battery voltage to the 5 V excitation level for the shoulder position sensor. The 5 V output to the shoulder sensor is pulsed at a duty cycle of, e.g., 1/16. Thus, the input from the shoulder position sensor to the controller 26 is received in pulses.

I. Therapetic Functional Neuromuscular Stimulation Using a Universal External Controller The firmware of the universal external controller 26 can be programmed for use in association with other components to perform other neuromuscular stimulation functions. For example, the universal external controller 26 can be used to provide therapeutic exercise and pain relief for stroke rehabilitation and surgical speciality applications, including shoulder subluxation, gait training, dysphagia, tenolysis, orthopedic shoulder, and arthroplasty.

Details of the treatment of shoulder subluxation by neuromuscular stimulation are set forth in copending U.S. patent application Ser. No. 09/089,994, filed Jun. 3, 1998 and entitled "Percutaneous Intramuscular Stimulation System" and copending U.S. patent application Ser. No. 09/755,871, filed Jan. 6, 2001 and entitled "Treatment of Shoulder Dysfunction Using a Percutaneous Intramuscular Stimulation System," both of which are incorporated herein by reference.

II. Representative Uses of the Universal External Controller

The universal external controller 26 as described herein incorporates several fundamental features that address convenience, flexibility, and ease of use.

By way of example, these features include:

(i) The controller 26 can be worn on the users body by virtue of it having a low weight and size.

(ii) The user can be enabled to modify parameters, such as how to control the system, the type and degree of exercise they undertake, and the type and degree of stimulus parameters they use for their stimulation function.

(iii) The utilization of cell phone battery technology makes the service, maintenance, and usage of the system more "consumer-like" and therefore easier to understand and use.

(iv) The controller 26 isolates the user from ever having to connect the system directly to any source of power or communication link. The system uses the rechargeable battery as its sole power source and the infrared link as a communications port to a computer.

(v) The controller 26 enables an extremely flexible control-input port that allows for,
1. Wireless communication (900 mghz)
   2. Proportional input signals (shoulder control)
   3. Natural signals generated by the body (EMG, ENG, EEG)
   4. A direct contact switch (on-off)

(vi) The controller 26 can support simultaneous control of two independent RF based implantable pulse generators (e.g., motor-control, and/or bladder/bowel control, and/or erection control function).

(vii) The controller 26 can communicate to any RF-based implantable pulse generators. Thus, the controller 26 can be easily integrated into an existing RF-based stimulation system.

(viii) The controller 26 can be programmed by a host computer, or be programmed directly by the user or a trained technician, without the need of an external host computer.

The following Examples are provided to exemplify the convenience, flexibility, and ease of use of a controller 26 that embodies features of the invention.

EXAMPLE 1

Different Selectable Neuromuscular Functions It has already been explained how the controller 26 can enable individual selection of different functional neuromuscular stimulation functions, e.g., the finger-grasp function, or the standing function, or the bladder and bowel control function.

The controller 26 can also be configured to provide these and other different neuromuscular functions concurrently. For example, using the menu-driven interface of the controller 26, as previously described, the user can select to implement a standing function concurrently with a bladder and bowel control function. In this arrangement, e.g., a user could affect concurrent neuromuscular stimulation to enable micturation while in a standing position. In the arrangement, the controller 26 receives control signals through one input to affect the operation of the standing function (e.g., a remote push-button control coupled to the input, or a push button programmed for this purpose on the user interface panel of the universal external controller 26 itself) while receiving other control signals through another input to affect operation of the bladder and bowel control function (e.g., another remote push-button control coupled to the other input, or another push button on the controller 26 programmed to accomplish this purpose). Concurrently, the controller 26 generates one stimulation output to the receiver/stimulator 18(2) for the standing function, while generating another, different stimulation output to the receiver/stimulator 18(3) for the bladder and bowel control function. In this arrangement, the controller 26 concurrently supports different control signal inputs and different stimulation outputs to different stimulation assemblies.

The controller 26 can be further configured to concurrently provide an additional finger-grasp function, based upon control signal input received by the controller 26 from e.g., a shoulder position sensor, and a stimulation output generated by the controller 26 to the receiver/stimulator 18(1) for the finger-grasp function. These concurrent, multiple stimulation functions make possible normal user control over the bladder and bowel function, while standing. Selection of the bladder and bowel control function concurrent with the selection of the finger-grasp function can also be accomplished, without selection of the standing function, to provide normal control over the bladder and bowel function while in a seated position.

As another example, concurrent selection of the finger-grasp function and the standing function would enable the user to grasp objects while in a standing position. Concurrent selection of these two functions would also allow the user to ambulate while carrying an object grasped in the user's fingers. Again, normal control over these functions is thereby provided.

EXAMPLE 2

Controller with Different Control Signal Sources

As previously explained, the universal external controller 26 can accommodate input from a variety of external control sources, such as myoelectric surface electrodes, remote control switching devices, reed switches, and push buttons on the user interface panel of the universal external controller 26 itself. External control sources can be coupled to the universal external controller 26 by direct (i.e., cable) connection, or by wireless link (e.g., 900 MHz). These different control signal sources can be selected for operation concurrently to achieve different, concurrent stimulation functions (as the preceding Example 1 demonstrates). These different control sources can also achieve the same stimulation function based upon different source inputs.

For example, the user can choose to affect the standing function, e.g., by operation of a remote push-button control, or a reed switch, or a push button programmed for this purpose on the universal external controller 26 itself. In addition, the user can also provide a designated care partner with a remote control switch to affect the standing function independently of the user, either by wireless transmission of a control signal or by a cable connection. Thus, for example, while the user holds of an ambulation assistance device, such as a walker, the care partner can remotely affect the standing function for the user, so that the user can be lifted to a standing position while the assistance device lends ancillary support and stability. Conversely, the care partner can remotely affect the termination of the standing function, so that the user can return to a seated position while the assistance device lends ancillary support and stability.

Various features of the invention are set forth in the following claims.

We claim:

1. A controller to provide functional neuromuscular stimulation comprising
    a housing,
    an output device carried by the housing that can be coupled to an electrode, a microprocessor carried by the housing coupled to the output device including a processing element operative to generate a signal pattern to an electrode to control at least one neuromuscular stimulation function, and a battery carried by the housing and coupled to the microprocessor to power the processing element, the signal pattern generated by the processing element comprising command signals transmitted in a periodic succession of energy pulses to conserve battery life.

2. A controller according to claim 1 wherein each energy pulse includes a stimulus phase during which the command signals are transmitted.

3. A controller according to claim 1 wherein each command signal includes a sequence of periodic pulses to identify an electrode channel and a set stimulation amplitude command for the identified electrode channel.

4. A controller according to claim 1 wherein each command signal includes a sequence of periodic pulses to identify an electrode channel and a set stimulation duration command for the identified electrode channel.

5. A controller according to claim 1 wherein each command signal includes a sequence of periodic pulses to identify an electrode channel, a set stimulation amplitude command for the identified electrode channel, and a set stimulation duration command for the identified electrode channel.

6. A controller according to claim 1 wherein the sequence of periodic pulses comprises an energy on period, an energy off period, and gaps between successive energy on and energy off periods.

7. A controller according to claim 1 wherein by number and sequence of gaps a code is expressed that identifies an electrode channel, a set stimulation amplitude command for the identified electrode, and a set stimulation duration command for the identified electrode.

8. A controller according to claim 1 wherein each command signal includes a sequence of periodic pulses expressing a code.

9. A controller according to claim 8 wherein the sequence of periodic pulses comprises an energy on period, an energy off period, and gaps between successive energy on and energy off periods, the code being expressed by number and sequence of the gaps.

10. A controller according to claim 8 wherein the code identifies an electrode channel.

11. A controller according to claim 8 wherein the code identifies a set stimulation amplitude command.

12. A controller according to claim 8 wherein the code identifies a set stimulation duration command.

13. A controller according to claim 1 wherein the periodic succession of energy pulses comprises modulated radio frequency waves.

14. A controller to provide functional neuromuscular stimulation comprising a housing, an output device carried by the housing that can be coupled to an electrode, a signal source to generate a control signal, an input device carried by the housing to receive the control signal generated by the signal source, a microprocessor carried by the housing coupled to the output device and the input device including a processing element operative to generate a signal pattern to an electrode to control at least one neuromuscular stimulation function in response to a control signal received from the input device, and a battery carried by the housing and coupled to the microprocessor to power the processing element, the control signal generated by the signal source comprises a periodic succession of pulses to conserve battery life.

15. A controller according to claim 14 wherein the signal pattern generated by the processing element comprises command signals transmitted in a periodic succession of energy pulses to conserve battery life.

16. A method of providing functional neuromuscular stimulation using a controller as defined in claim 1 or 14.

17. A method of providing functional neuromuscular stimulation comprising the steps of providing a controller as defined in claim 1 or 14, and operating the controller to affect at least one motor function.

18. A method of providing functional neuromuscular stimulation comprising the steps of providing a controller as defined in claim 1 or 14, and operating the controller to affect a bladder or bowel control function.

19. A method of providing functional neuromuscular stimulation comprising the steps of providing a controller as defined in claim 1 or 14, and operating the controller to affect an erection control function.

20. A method of providing functional neuromuscular stimulation comprising the steps of providing a controller as defined in claim 1 or 14, and operating the controller to concurrently affect at least one motor function and at least one other neuromuscular stimulation function.

21. A method of providing functional neuromuscular stimulation comprising the steps of providing a controller as defined in claim 1 or 14, and operating the controller to affect at least two neuromuscular stimulation functions.

* * * * *